United States Patent
Haughey et al.

(10) Patent No.: US 11,759,466 B2
(45) Date of Patent: Sep. 19, 2023

(54) INHIBITION OF NSMASE FOR THE TREATMENT OF HUMAN IMMUNODEFICIENCY VIRUS INFECTION

(71) Applicant: The Johns Hopkins University, Baltimore, MD (US)

(72) Inventors: Norman Haughey, Baltimore, MD (US); Barbara Slusher, Kingsville, MD (US); Camilo Rojas, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/977,309

(22) PCT Filed: Mar. 1, 2019

(86) PCT No.: PCT/US2019/020258
§ 371 (c)(1),
(2) Date: Sep. 1, 2020

(87) PCT Pub. No.: WO2019/169249
PCT Pub. Date: Sep. 6, 2019

(65) Prior Publication Data
US 2021/0000833 A1    Jan. 7, 2021

Related U.S. Application Data

(60) Provisional application No. 62/636,901, filed on Mar. 1, 2018.

(51) Int. Cl.
A61K 31/51       (2006.01)
A61P 31/18       (2006.01)
(Continued)

(52) U.S. Cl.
CPC ........ *A61K 31/519* (2013.01); *A61K 31/4178* (2013.01); *A61K 31/5025* (2013.01); *A61P 31/18* (2018.01)

(58) Field of Classification Search
CPC .............. A61K 31/519; A61K 31/4178; A61K 31/5025; A61P 31/18
See application file for complete search history.

(56) References Cited

U.S. PATENT DOCUMENTS

2005/0203155 A1    9/2005   Salassidis et al.
2008/0045536 A1*   2/2008   Vaccaro ................. A61P 31/18
                                                                    544/236
(Continued)

FOREIGN PATENT DOCUMENTS

WO    2007/038314 A2    4/2007
WO    2009/140128 A2    11/2009
(Continued)

OTHER PUBLICATIONS

Kosaka et al., Neutral Sphingomyelinase 2 (nSMase2)-dependent Exosomal Transfer of Angiogenic MicroRNAs Regulate Cancer Cell Metastasis, J Biol Chem, (2013), 288 (15), pp. 10849-10859.
(Continued)

*Primary Examiner* — Shengjun Wang
(74) *Attorney, Agent, or Firm* — Casimir Jones, S.C.; Jeffrey W. Childers

(57) ABSTRACT

Methods for treating a Human Immunodeficiency Virus (HIV) infection comprising administering to a subject in need of treatment thereof an effective amount of a small molecule nSMase2 inhibitor.

14 Claims, 14 Drawing Sheets

(51) Int. Cl.
  *A61K 31/519*   (2006.01)
  *A61K 31/4178*  (2006.01)
  *A61K 31/5025*  (2006.01)

(56) References Cited

U.S. PATENT DOCUMENTS

| | | | |
|---|---|---|---|
| 2012/0220581 A1 | 8/2012 | Pastor-Fernandez et al. | |
| 2016/0143884 A1 | 5/2016 | Orlemans et al. | |
| 2020/0190089 A1* | 6/2020 | Slusher | C07D 487/04 |

FOREIGN PATENT DOCUMENTS

| | | |
|---|---|---|
| WO | 2011/147753 A1 | 12/2011 |
| WO | WO 2014/138692 | 9/2014 |
| WO | 2016/141381 A2 | 9/2016 |
| WO | 2018/129405 A1 | 7/2018 |
| WO | WO 2019/169247 | 9/2019 |

OTHER PUBLICATIONS

Asai et al., Depletion of Microglia and Inhibition of Exosome Synthesis Halt Tau Propagation, Nat Neurosci, (2015), 18 (11), pp. 1584-1593.

Badowski et al., New Antiretroviral Treatment for HIV, Infect Dis Ther, (2016), 5 (3), pp. 329-352.

Berge et al., Pharmaceutical Salts, Journal of Pharmaceutical Science, (1977), 66 (1), pp. 1-19.

Bowes et al., Reducing safety-related drug attrition: the use of in vitro pharmacological profiling, Nat Rev Drug Discov, (2012), 11 (12), pp. 909-922.

Cutler et al., Evidence that Accumulation of Ceramides and Cholesterol Esters Mediates Oxidative Stress-Induced Death of Motor Neurons in Amyotrophic Lateral Sclerosis, Ann Neurol, (2002), 52 (4), pp. 448-457.

Dickens et al., Astrocyte-shed extracellular vesicles regulate the peripheral leukocyte response to inflammatory brain lesions, Sci Signal, (2017), 10 (473), eaai7696.

Figuera-Losada et al., Cambinol, a novel inhibitor of neutral sphingomyelinase 2 shows neuroprotective properties, PLoS One, (2015), 10 (5), e0124481.

Haughey et al., Perturbation of Sphingolipid Metabolism and Ceramide Production in HIV-Dementia, Ann Neurol, (2004), 55 (2), pp. 257-267.

Horres et al., The Roles of Neutral Spingomyelinases in Neurological Pathologies, Neurochem Res, (2012), 37 (6), pp. 1137-1149.

Jana et al., Fibrillar Amyloid-Beta-Activated Human Astroglia Kill Primary Human Neurons Via Neutral Sphingomyelinase: Implications for Alzheimer's Disease, J Neurosci, (2010), 30 (38), pp. 12676-12689.

Jana et al., Human Immunodeficiency Virus Type 1 gp120 Induces Apoptosis in Human Primary Neurons through Redox-Regulated Activation of Neutral Sphingomyelinase, J Neurosci, (2004), 24 (43), pp. 9531-9540.

Jana et al., Sphingolipids in Multiple Sclerosis, Neuromol Med, (2010), 12 (4), pp. 351-361.

Jana et al., Ceramide and Neurodegeneration: Susceptibility of Neurons and Oligodendrocytes to Cell Damage and Death, Journal of the Neurological Sciences, (2009), 278 (1-2), pp. 5-15.

Kull et al., Mixtures of quaternary ammonium compounds and long-chain fatty acids as antifungal agents, Applied Microbiology, (1961), 9 (6), pp. 538-541.

Luberto et al., Inhibition of Tumor Necrosis Factor-induced Cell Death in MCF7 by a Novel Inhibitor of Neutral Sphingomyelinase, J Biol Chem, (2002), 277 (43), pp. 41128-41139.

McCluskey et al., Inflammatory responses in the rat brain in response to different methods of intracerebral administration, J Neuroimmunol, (2008), 194 (1-2), pp. 27-33.

Mejdrova et al., Highly Selective Phosphatidylinositol 4-Kinase IIIBeta Inhibitors and Structural Insight Into Their Mode of Action, J. Med. Chem., (2015), 58 (9), pp. 3767-3793.

Rais et al., Discovery of 6-Diazo-5-oxo-l30 norleucine (DON) Prodrugs with Enhanced CSF Delivery in Monkeys: A Potential Treatment for Glioblastoma, J Med Chem, (2016), 59 (18), pp. 8621-8633.

Sala et al., Purine Analogs as Phosphatidylinositol 4-Kinase IIIBeta Inhibitors, Bioorg. Med. Chem. Lett., (2016), 26 (11), pp. 2706-2712.

Van Echten-Deckert et al., Sphingolipids: Critical Players in Alzheimer's Disease, Progress in Lipid Research, (2012), 51 (4), pp. 378-393.

Extended EP Search Report for EP19761104, dated Jan. 10, 2022, 10 pages.

* cited by examiner

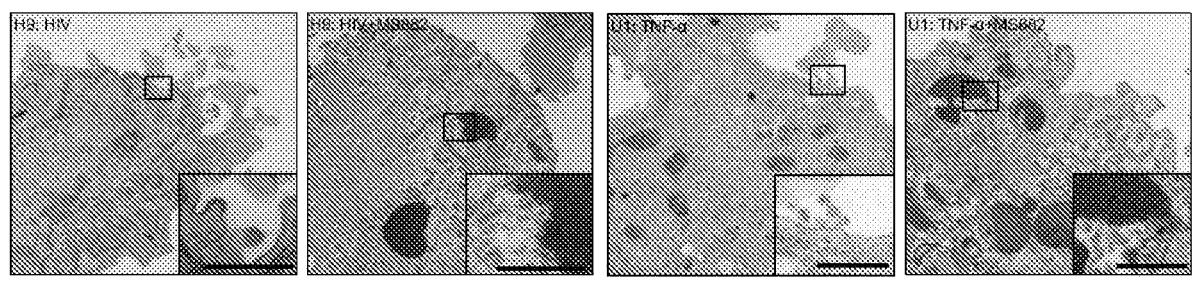
*Fig. 6A*  *Fig. 6B*

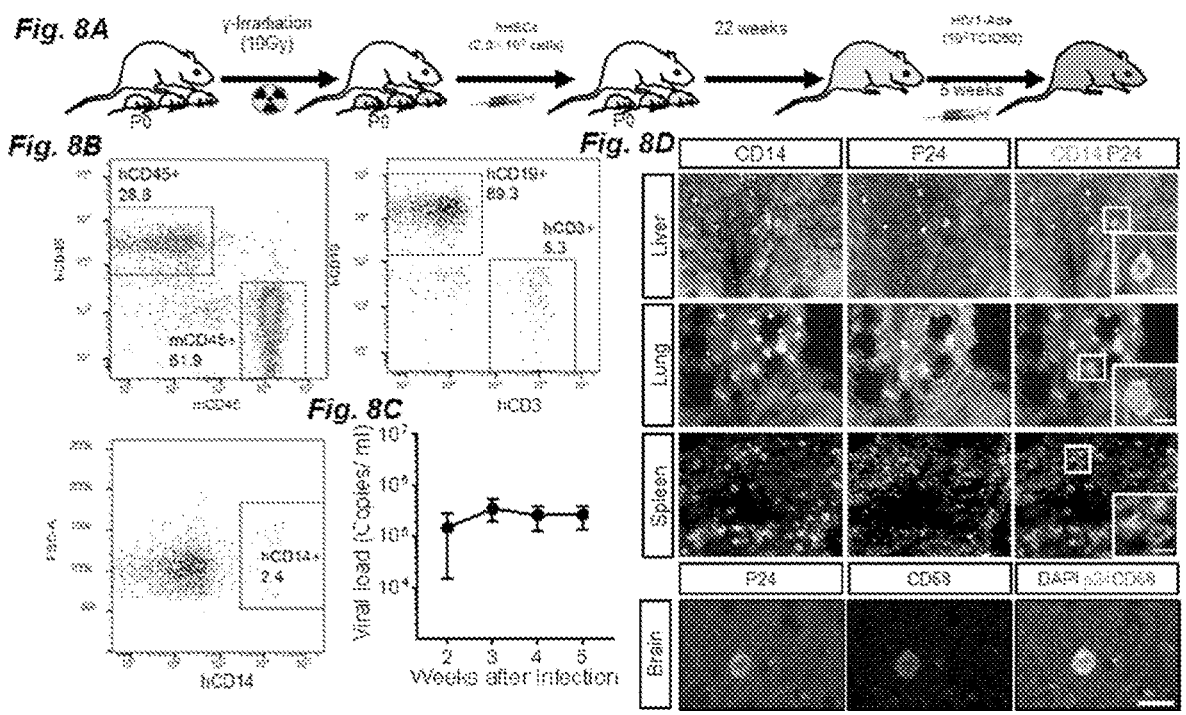

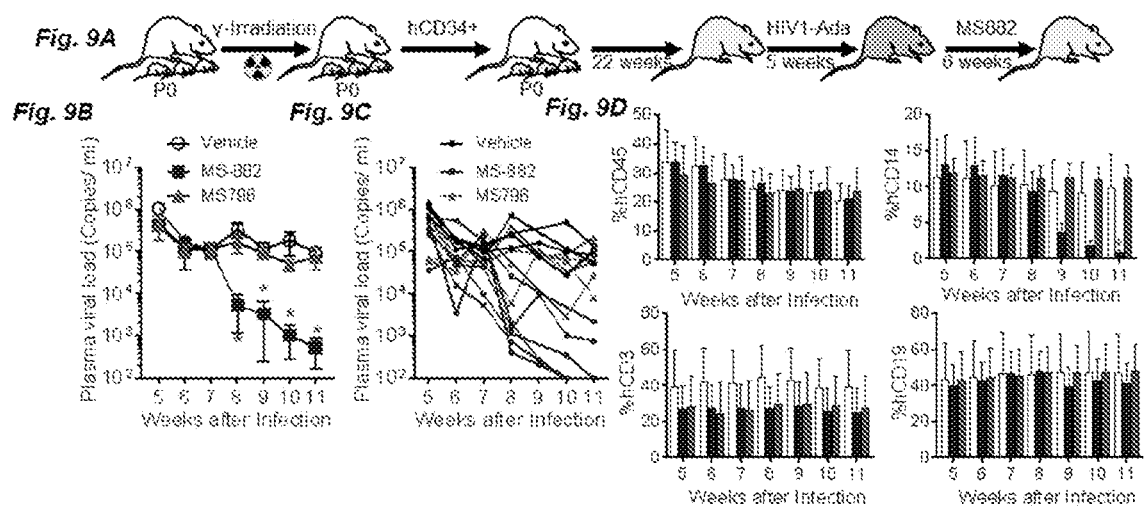

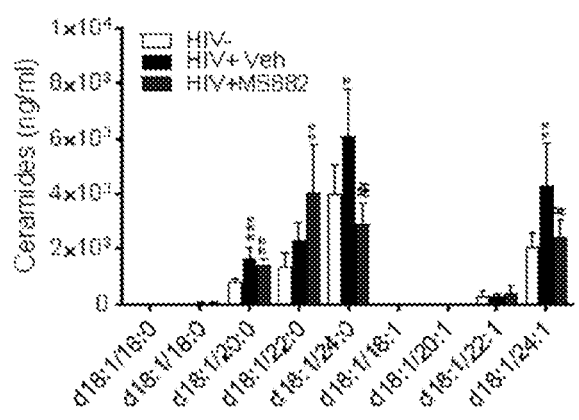 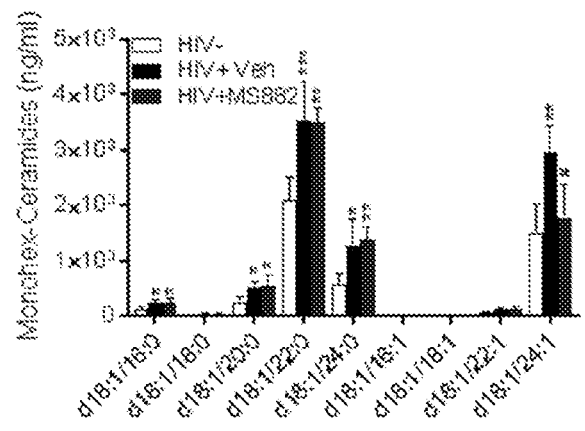
*Fig. 10A*  *Fig. 10B*

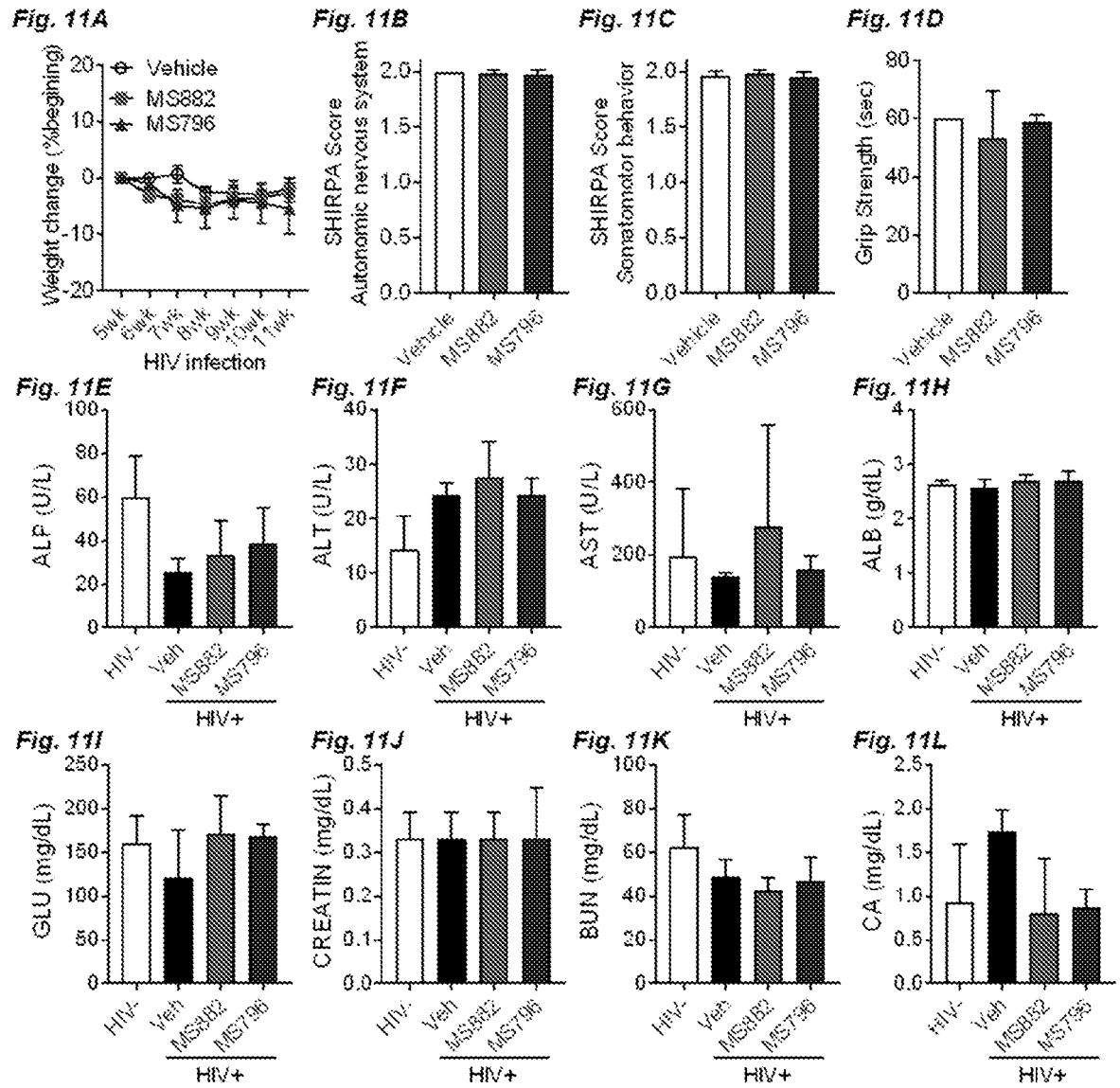

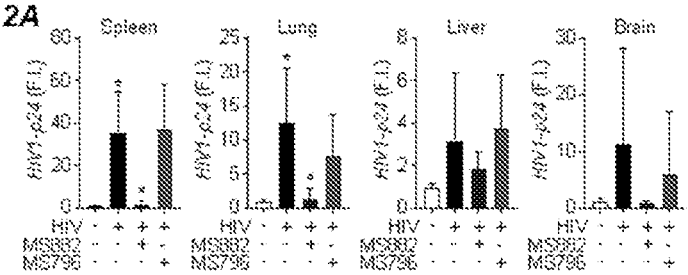
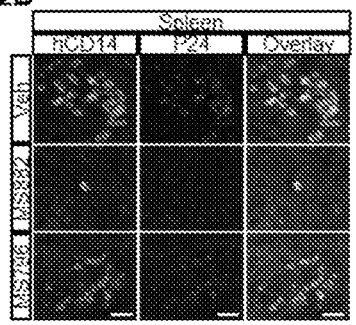
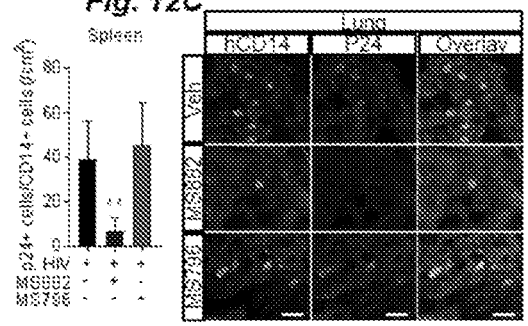
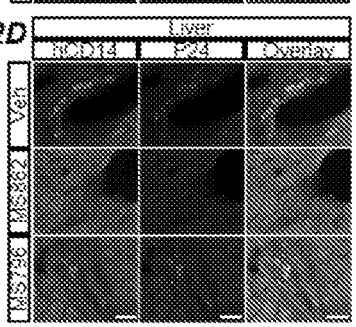
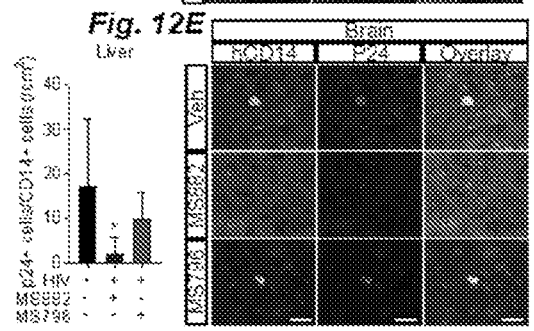
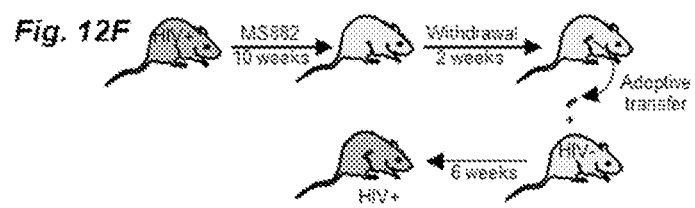
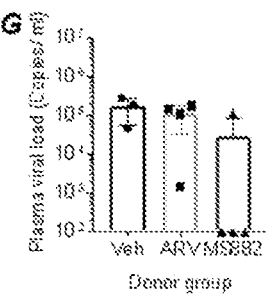

INHIBITION OF NSMASE FOR THE TREATMENT OF HUMAN IMMUNODEFICIENCY VIRUS INFECTION

FEDERALLY SPONSORED RESEARCH OR DEVELOPMENT

This invention was made with government support under grant numbers MH107659 and MH075673 awarded by the National Institutes of Health. The government has certain rights in this invention.

SEQUENCE LISTING

The text of the computer readable sequence listing filed herewith, titled "36522-252_SEQUENCE_LISTING_ST25", created Jan. 30, 2021, having a file size of 936 bytes, is hereby incorporated by reference in its entirety.

BACKGROUND

The Human Immunodeficiency Virus (HIV) is a retrovirus that targets the immune system. Individuals infected with HIV gradually become immune deficient and susceptible to other infectious agents and some cancers. Infection by HIV continues to be a major global health issue with approximately 36.7 million people living with HIV, and 1.8 million new infections each year. Without treatment, HIV infection is fatal to the vast majority of infected individuals.

Antiretroviral therapy (ART) was first introduced in the mid-1990s, and quickly advanced to combinational drug therapies. The simultaneous use of three drugs that inhibit different parts of the HIV life cycle (or cellular targets) is now standard therapy to treat HIV infection. By reducing HIV viral load in the body, ART has prolonged the average life-expectancy for individuals living with HIV and reduced the probability of transmitting the virus to sexual partners.

HIV evolves to become resistant to some drugs and there has been a considerable amount of new drug development to continue to combat HIV. Although many parts of the viral lifecycle have been targeted by ART, there is currently not a single drug to target viral budding. This is a critical part of the viral lifecycle in which HIV emerges from cells by budding outwards, using the host cellular membrane to enclose the viral capsid.

SUMMARY

The presently disclosed subject matter provides a method for treating a Human Immunodeficiency Virus (HIV) infection, the method comprising administering to a subject in need of treatment thereof an effective amount of an nSMase2 inhibitor of formula (I):

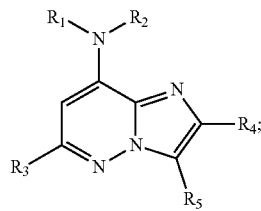

wherein:

$R_1$ and $R_2$ are each independently selected from substituted or unsubstituted alkyl or together with the nitrogen atom to which they are bound form a substituted or unsubstituted 5- or 6-membered heterocyclic ring;

$R_3$ is selected from the group consisting of H, substituted or unsubstituted alkyl, substituted or unsubstituted alkoxyl, substituted or unsubstituted thioalkyl, substituted or unsubstituted aryl, and halogen;

$R_4$ is selected from the group consisting of H, substituted or unsubstituted alkyl, and substituted or unsubstituted aryl;

$R_5$ is selected from the group consisting of H, halogen, substituted or unsubstituted alkyl, substituted or unsubstituted aryl, substituted or unsubstituted heteroaryl, and a substituted or unsubstituted multicyclic aryl or multicyclic heteroaryl ring;

under the proviso that if $R_1$ and $R_2$ together with the nitrogen atom to which they are bound are pyridinyl or morpholinyl, then $R_5$ cannot be H, halogen, or substituted or unsubstituted heteroaryl; and pharmaceutically acceptable salts thereof.

In particular aspects, the compound of formula (I) is:

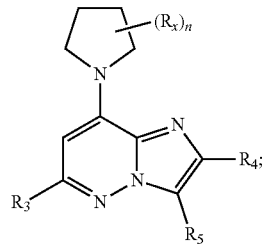

wherein:

n is an integer selected from the group consisting of 0, 1, 2, 3, 4, 5, 6, 7, and 8;

$R_x$ is selected from the group consisting of halogen, hydroxyl, substituted or unsubstituted alkoxyl, substituted or unsubstituted thioalkyl, cyano, amino, $—N_3$, substituted or unsubstituted aryl, substituted or unsubstituted cycloheteroalkyl, substituted or unsubstituted heteroaryl, $—X—(C=O)—C_{1-6}$ alkyl, wherein X is O or S, and $—NR_6R_7$, wherein $R_6$ is selected from the group consisting of H or substituted or unsubstituted $C_{1-6}$ alkyl; and $R_7$ is selected from the group consisting of $—C(=O)—(CR_yR_z)_m—R_8$, $—C(=O)—(CR_yR_z)_m—O—R_8$, $—C(=O)—O—(CR_yR_z)_m—R_8$, and $—S(=O)_2-R_9$, wherein each m is an integer selected from the group consisting of 0, 1, 2, 3, 4, 5, and 6, $R_y$ and $R_z$ are each independently H, alkoxyl, or halogen, $R_8$ and $R_9$ are each independently selected from the group consisting of substituted or unsubstituted alkyl, $—CF_3$, substituted or unsubstituted cycloalkyl, substituted or unsubstituted aryl, substituted or unsubstituted cycloheteroaryl, substituted or unsubstituted multicyclic aryl or heteroaryl ring, and $NR_{10}R_{11}$, wherein $R_{10}$ and $R_{11}$ are each independently selected from the group consisting of H, substituted or unsubstituted $C_{1-6}$ alkyl, and substituted or unsubstituted aryl.

In more particular aspects, the compound of formula (I) is:

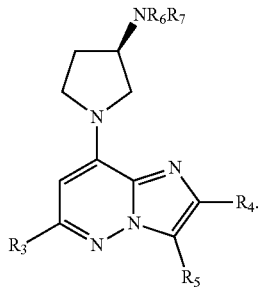

In yet more particular aspects, the compound of formula (I) is:

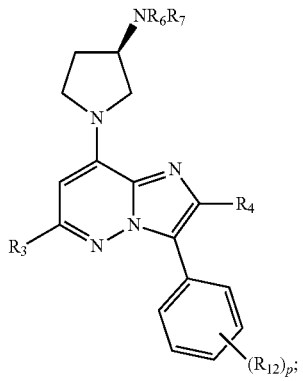

wherein:
p is an integer selected from the group consisting of 0, 1, 2, 3, 4, and 5;
each $R_{12}$ is independently selected from the group consisting of substituted or unsubstituted alkyl, hydroxyl, alkoxyl, halogen, cyano, amino, —$CF_3$, —O—$CF_3$, substituted or unsubstituted cycloheteroaklyl, —$NR_{13}$ (C=O)$R_{14}$, —S(=O)$_2$—$R_{15}$, —S(=O)$_2$—$NR_{15}R_{16}$, —$SR_{16}$, —C(=O)—$R_{17}$, —C(=O)—O—$R_{18}$, and —C(=O)—$NR_{19}R_{20}$, wherein $R_{13}$ is selected from the group consisting of H or substituted or unsubstituted $C_{1-6}$ alkyl, $R_{14}$ is substituted or unsubstituted $C_{1-6}$ alkyl or —O—$R_{21}$, and $R_{15}$, $R_{16}$, $R_{17}$, $R_{18}$, $R_{19}$, $R_{20}$, $R_{21}$ are each independently H or substituted or unsubstituted $C_{1-6}$ alkyl.

In other aspects, the presently disclosed subject matter provides a method for treating a Human Immunodeficiency Virus (HIV) infection, the method comprising administering to a subject in need of treatment thereof an effective amount of 2,6-dimethoxy-4-(5-phenyl-4-thiophen-2-yl-1H-imidazol-2-yl)-phenol (DPTIP):

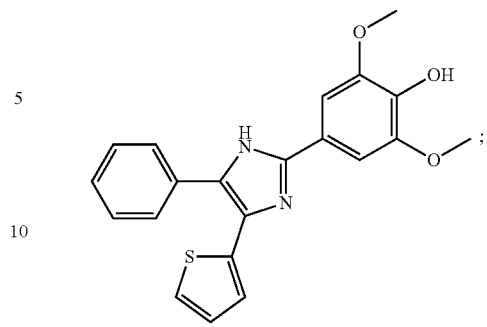

or a pharmaceutically acceptable salt thereof.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 1A:
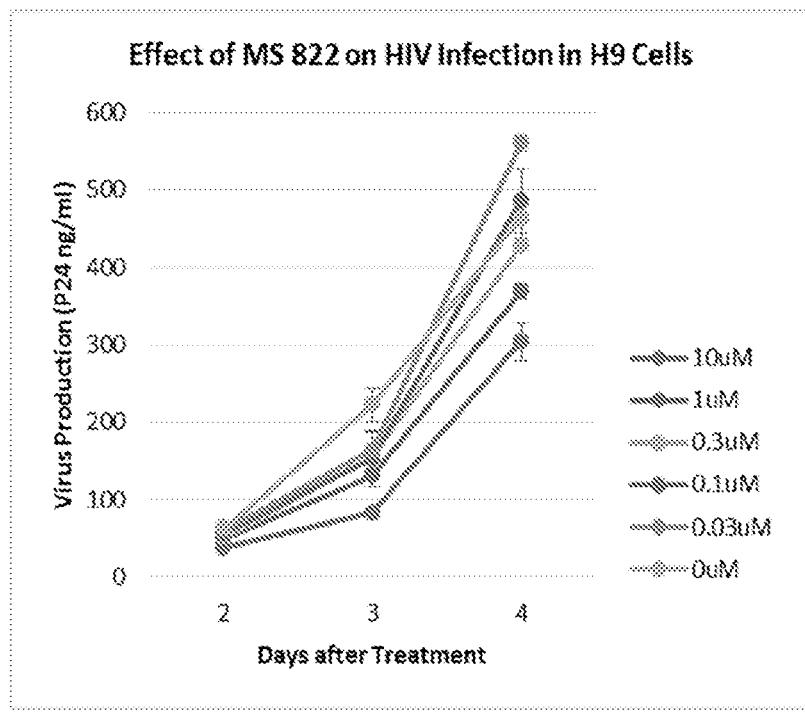
Figure 1B:
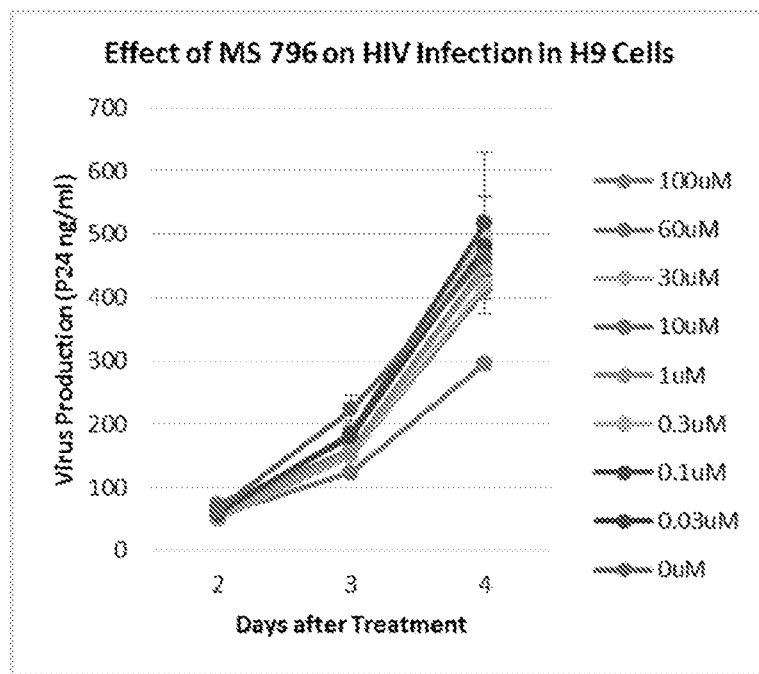
Figure 2A:
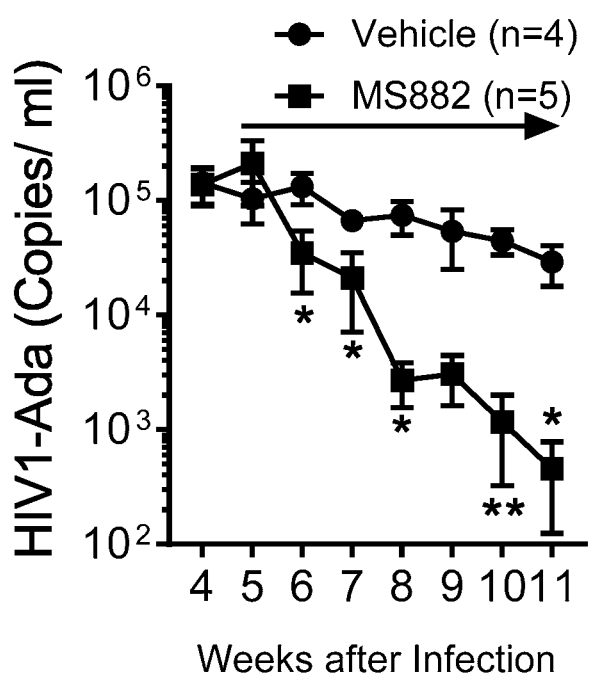
Figure 2B:
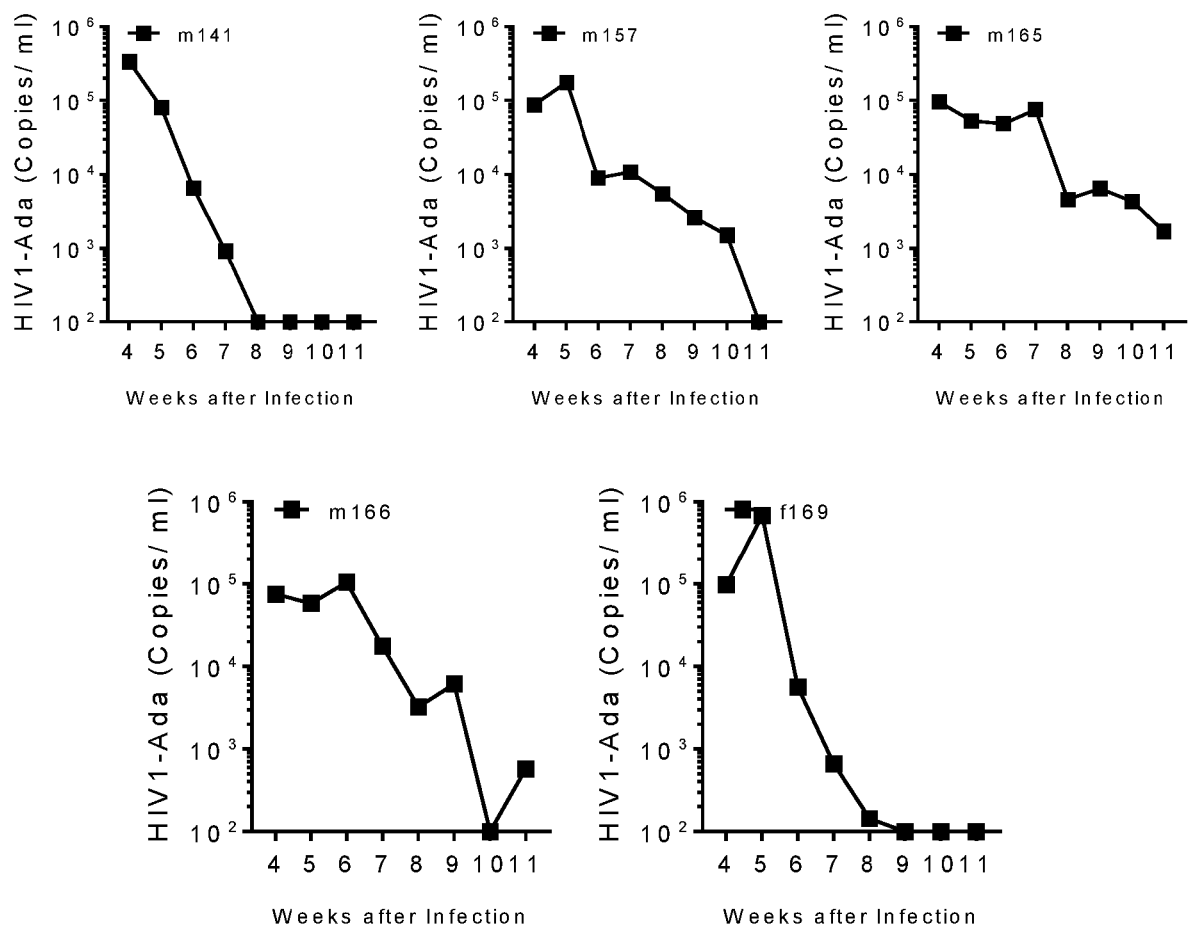
Figure 3A:
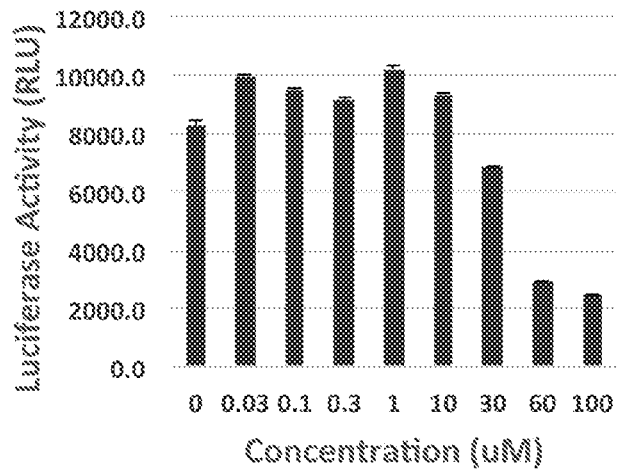
Figure 3B:
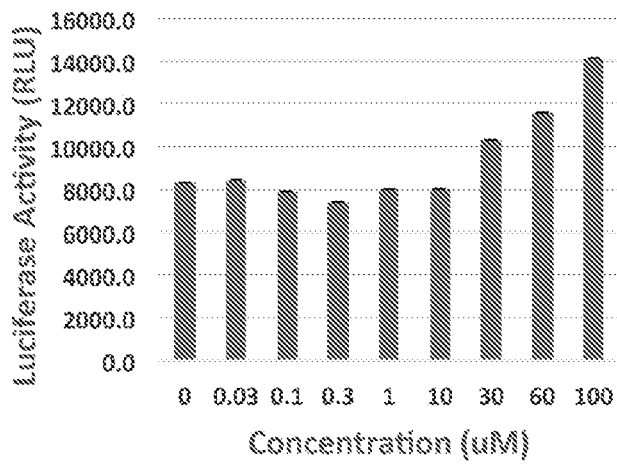
Figure 4A:
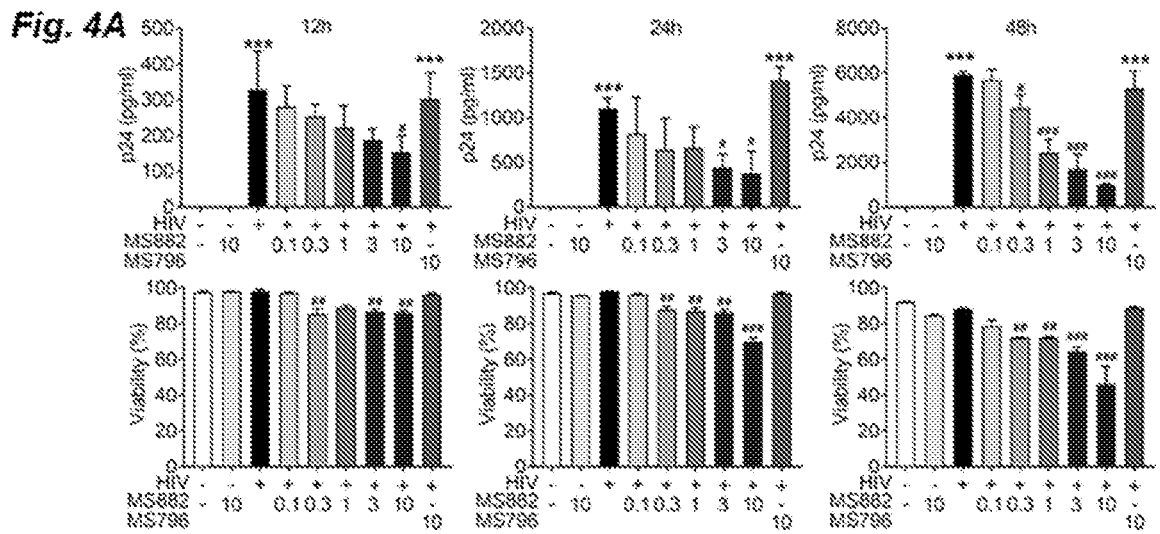
Figure 4B:
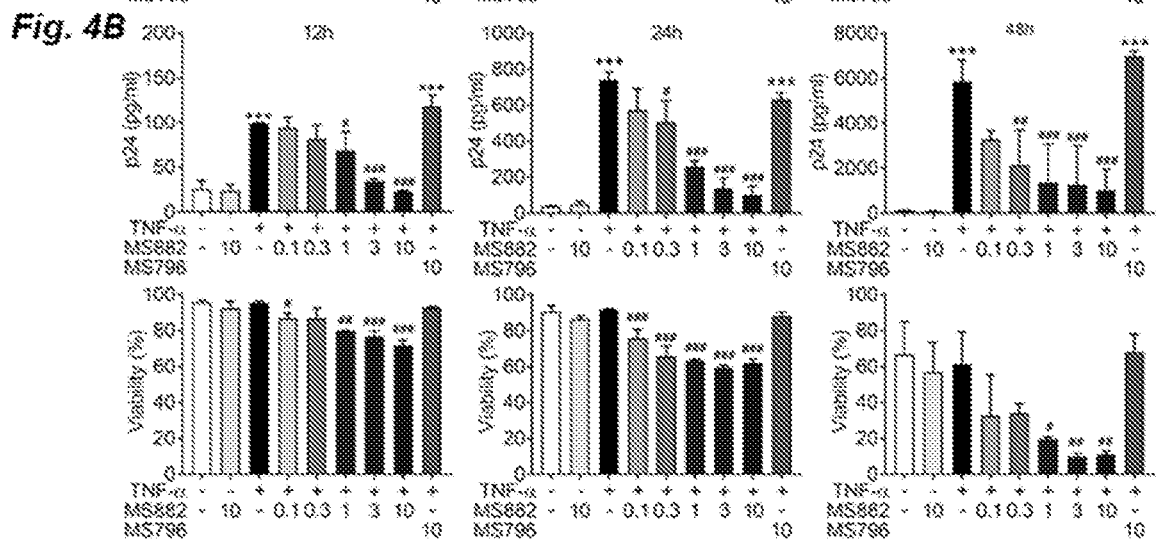
Figure 4C:
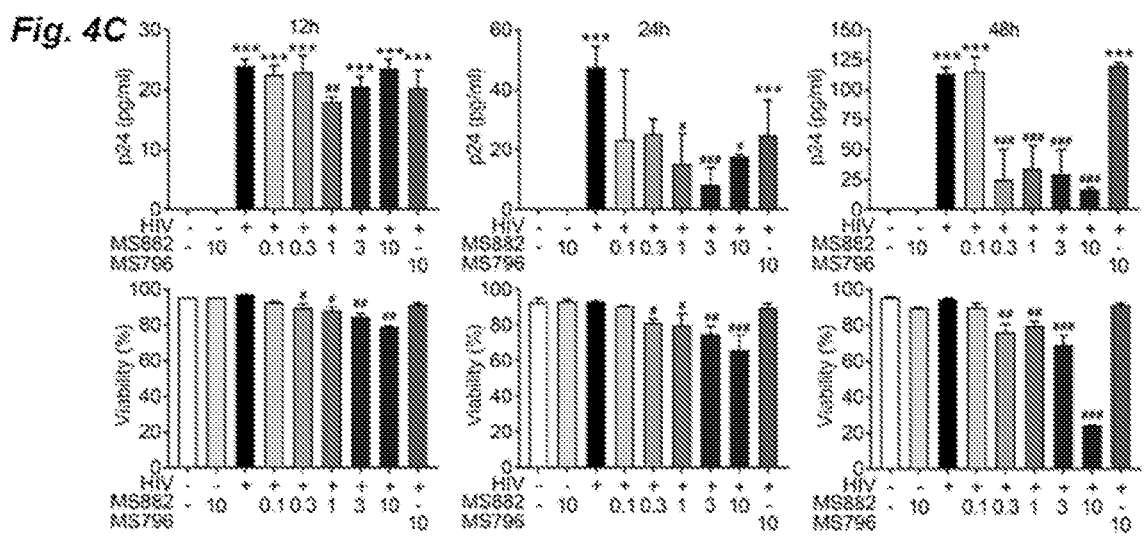
Figure 5A:
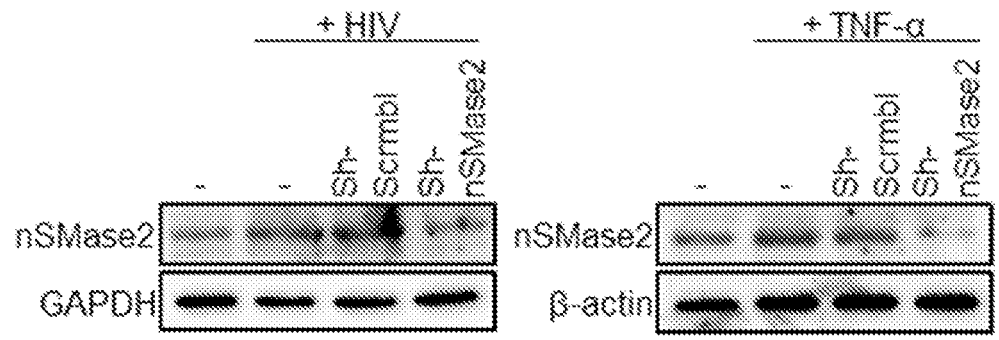
Figure 5B:
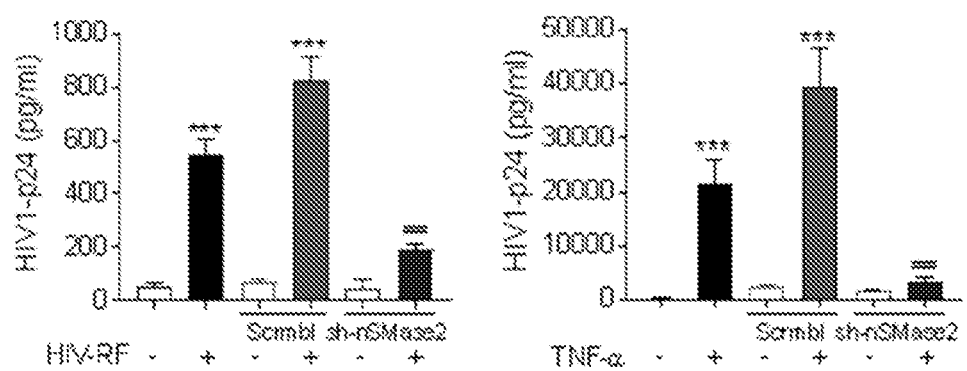
Figure 5C:
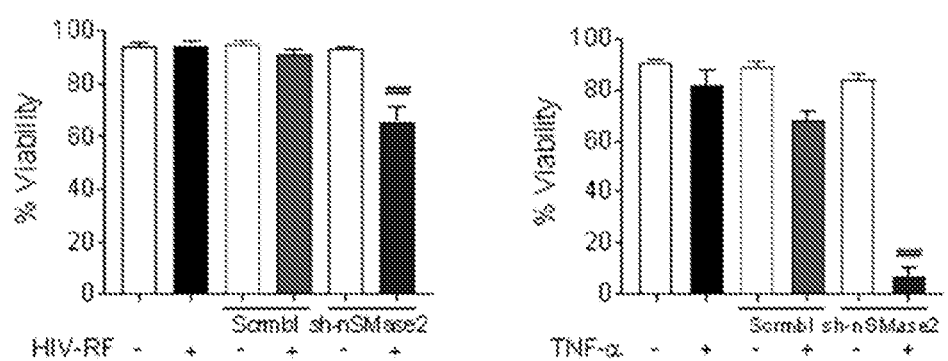
Figure 7A:
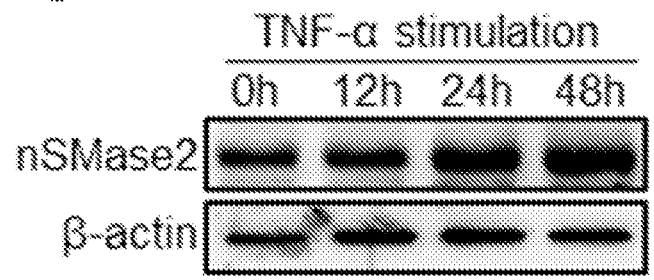
Figure 7B:
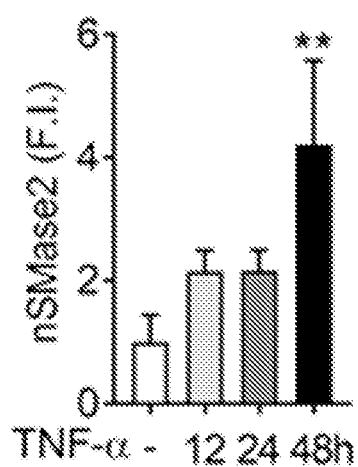
Figure 7C:
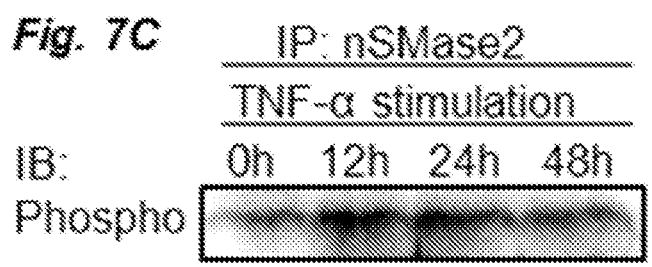
Figure 7D:
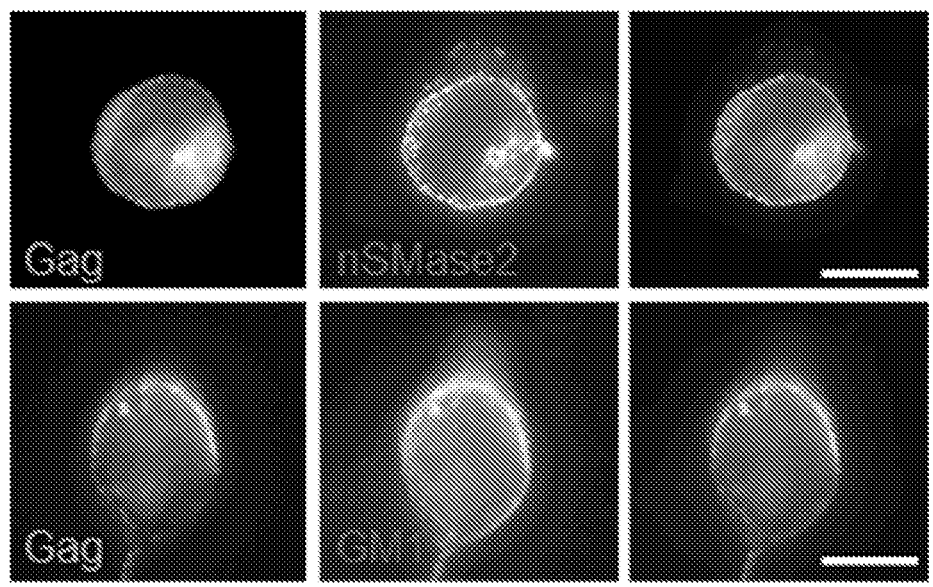
Figure 7E:
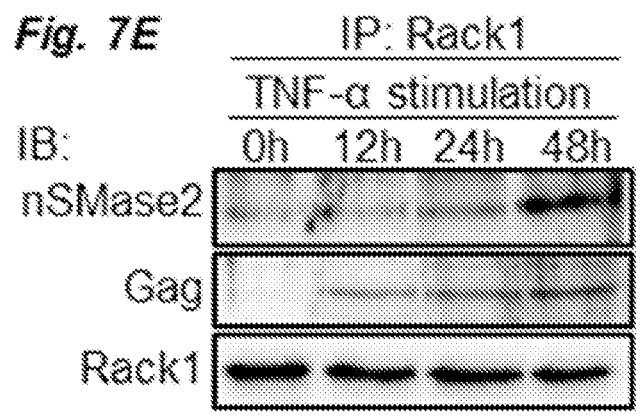
Figure 13A:
Figure 13B:
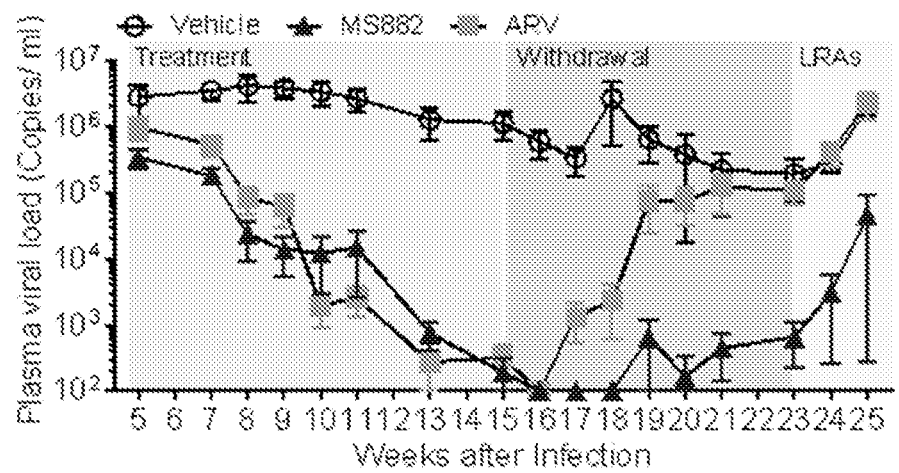
Figure 13C:
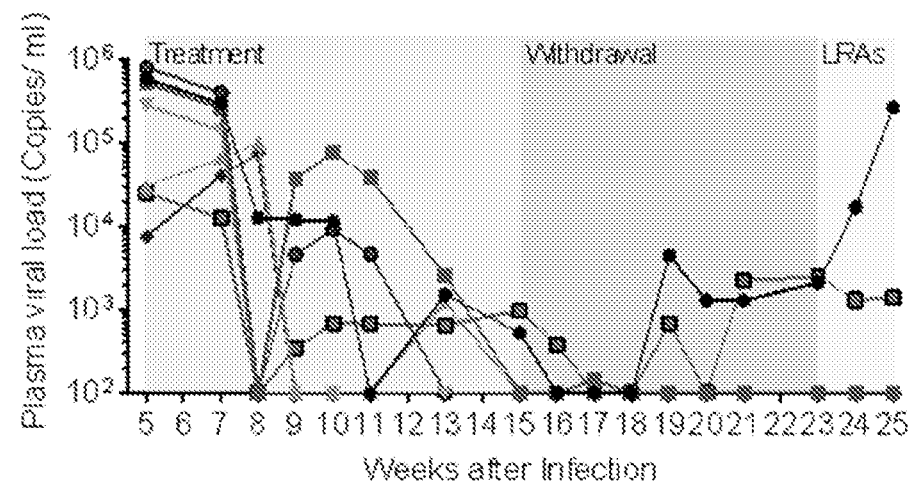

Having thus described the presently disclosed subject matter in general terms, reference will now be made to the accompanying Figures, which are not necessarily drawn to scale, and wherein:

FIG. 1A and FIG. 1B demonstrate that nSMase blocks HIV replication. FIG. 1A shows the novel nSMase2 inhibitor MS822 (31) dose-dependently reduced HIV replication in H9 cells infected with HIV as determined by P24 ELISA of culture supernatants. FIG. 1B shows the inactive analog MS796 (1-PROV) did not dose-dependently reduce HIV replication. Data are mean±SEM of n=3 per condition. ANOVA with Tukey post hoc comparisons;

FIG. 2A and FIG. 2B demonstrate that inhibition of nSMase reduces viral load in HIV-infected humanized mice. FIG. 2A is summary data showing that daily intraperitoneal administrations of the nSMase2 inhibitor MS822 (31) reduced plasma HIV viral load over the indicated time period. FIG. 2B is the plasma viral load response to treatment with MS822 (31) shown for individual mice in the study. MS822 (31) reduced plasma HIV viral load to below detectable levels in 3 out of 5 mice tested. Data are mean±SEM of n=3 per condition. ANOVA with Tukey post hoc comparisons;

FIG. 3A and FIG. 3B demonstrate that inhibition of nSMase does interfere with viral entry or transcription. FIG. 3A shows that treatment of H9 cells with the nSMase inhibitor MS882 (31) reduced luciferase activity in TZM/Bl cells at the highest doses tested. FIG. 3B shows that the inactive analog MS796 (1-PROV) did not reduce luciferase activity in TZM/Bl cells, but may have increased activity at the highest doses tested. These data suggest that inhibition of nSMase2 with MS822 (31) does not modify HIV entry or transcription;

FIG. 4A, FIG. 4B, and FIG. 4C show inhibition of neutral sphingomyelinases suppressed HIV-replication. Quantification of HIV replication (p24 levels) in medium (top) and cell viability (bottom) of H9 cells (FIG. 4A), U1 cells (FIG. 4B), and human primary CD4+ cells (FIG. 4C) treated with nSMase2 inhibitor, MS882 (31). Cells were treated with various concentrations of MS882 (31) (0.1 μM-10 μM) or an inactive structural analog of MS882 (31), e.g., MS796 (1-PROV) (10 μM) following HIV infection (H9 cells, HIV-RF, 100 ng/ml; primary human CD4+ cells, HIV-MN, 200 ng/mL), or TNF-α treatment (U1 cells, 500 ng/mL). HIV replication and cell viability were measured at 12 h, 24 h, and 48 h after treatment of MS882 (31). Data are mean±S.D of n=3 per independent experiments/condition. *=$p<0.05$; =$p<0.01$; *=$p<0.001$ compared to uninfected control (H9 cells, primary human CD4+ cells), or non-TNFα-induced control (U1 cells). #=$p<0.05$; ##=$p<0.01$; ###=$p<0.001$ compared to HIV-infected or TNF-α-induced cells. One-Way ANOVA with Tukey post-hoc comparisons;

FIG. 5A, FIG. 5B, and FIG. 5C show genetic knockdown of nSMase2 suppressed HIV-replication in H9 cells and U1 cells with selective killing on HIV-replication. (FIG. 5A) Representative immunoblots of H9 cells (left) and U1 cells (right) delivered with lentivirus expressing sh-RNA for nSMase2 (Sh-nSMase2) or scrambled RNA (Sh-scrmbl) at 48 h after HIV infection (H9 cells) or TNF-α stimulation (500 ng/mL, U1 cells). Quantification of p24 levels in medium (FIG. 5B) and viability (FIG. 5C) from H9 cells (left) and U1 cells (right) delivered with Sh-scrmbl or Sh-nSMase2 at 48 h after HIV infection (100 ng/mL) or TNF-α stimulation (500 ng/mL, U1 cells). Data are mean±S.D of n=3 per independent experiments/condition. ***=$p<0.001$ compared to uninfected or uninduced cells; ###=$p<0.001$ compared to HIV-infected or TNF-α induced cells. One-Way ANOVA with Tukey post-hoc comparisons;

FIG. 6A and FIG. 6B demonstrate that inhibition of nSMase2 triggered endo/lysosomal stress-induced cell death. Representative electron microscope images of H9 cells (FIG. 6A) and U1 cells (FIG. 6B) treated with MS882 (31) (10 μM) for 6 h following HIV infection (H9 cells) or TNF-α stimulation (U1 cells). Phenotypically immature virus were emerged from HIV-infected cells, and mature virions in the extracellular space. Treatment of MS882 (31) induced enlarged endolysosomal compartments engorged with EM-dense debris consistent with proteinaceous materials. Scale bar, 1 μm;

FIG. 7A, FIG. 7B, FIG. 7C, FIG. 7D, and FIG. 7E demonstrate that nSMase2 expression and activation are increased with HIV-infection. nSMase2 is closely associated with HIV1-Gag during HIV assembly/budding. Representative immunoblots (FIG. 7A) and quantification (FIG. 7B) of time-dependent increased expression of nSMase2 in U1 cells stimulated with TNF-α (500 ng/mL) for 12 h, 24 h, and 48 h. (FIG. 7C) Representative immunoblots for activation of nSMase2 in U1 cells stimulated with TNF-α (500 ng/mL) for 12 h, 24 h, and 48 h. Total proteins (300 μg) were immunoprecipitated with anti-nSMase2 antibody and blotted with anti-phospho antibody. (FIG. 7D) Representative fluorescent images of U937 cells transfected with Gag-iGFP. The cells were stained with anti-nSMase2 antibody (Red, top) or CTX-555 for GM1 (Red, bottom), indicating that nSMase2 is colocalized with Gag in GM1+ membrane microdomains. (FIG. 7E) Representative immunoblots for interaction of Rack1 with nSMase2 and HIV1-gag in U1 cells stimulated with TNF-α (500 ng/mL) for 12, 24, and 48 h. Total proteins (50 μg) were immunoprecipitated with anti-Rack antibody and blotted with anti-nSMase2, -Gag, and -Rack1 antibody, indicating that Rack1 mediated nSMase2-Gag interaction during HIV assembly/budding. Data are mean±S.D of n=3 per independent experiments/condition. **=$p<0.01$ compared to non-TNFα-induced control U1 cells. One-Way ANOVA with Tukey post-hoc comparisons. Scale bar, 10 μm;

FIG. 8A, FIG. 8B, FIG. 8C, and FIG. 8D show generation of humanized mice and characterization of HIV infection. (FIG. 8A) Schematic illustration for generation of humanized mice (hu-NSG). NOD.Cg-Prkdcscid Il2rgtm1Wj1/SzJ (NSG-mice) were exposed to γ-irradiation (10 Gy, 137 Ce source) at p0, followed by intrahepatic injection of $2.0 \times 10^5$ human umbilical cord blood-derived CD34+ cells. At twenty-two weeks of humanization the mice were infected with HIV1-Ada (10,000 TCID50). (FIG. 8B) Representative plots by flow cytometry demonstrating reconstitution of human immune systems in hu-NSG. (FIG. 8C) Time-course plasma viremia in HIV-hu-NSG, indicating sustained viral replication in vivo. (FIG. 8D) Representative images of HIV+ (p24) human macrophages (CD14 or CD68) in liver, lung, spleen, and brain (hippocampus) of HIV-hu-NSG. Data are mean±S.D. Scale, 20 μm;

FIG. 9A, FIG. 9B, FIG. 9C, and FIG. 9D demonstrate that NSMase2 inhibitors selectively killed macrophages in HIV-infected humanized mice. (FIG. 9A) Schematic illustration for generation of humanized mice (hu-NSG). NOD.Cg-Prkdc$^{scid}$ Il2rg$^{tm1Wjl}$/SzJ (NSG) reconstituted with human umbilical cord blood-derived CD34+ cells were infected with HIV1-Ada with 10,000 TCID50 at 22 weeks of age. (FIG. 9B) Five weeks after HIV infection, the mice were daily administered with MS882 (31) (blue, 10 mg/kg), MS796 (1-PROV) (red. 10 mg/kg) or vehicle (5% DMSO, 5% Tween-80 in saline, open circle) for 6 weeks (n=4-6 in each group). RNAs were extracted from plasma and viral load was calculated by quantitative RT-PCR. (FIG. 9C) Plasma viremia of each mice daily administered with MS882 (31) (blue), MS796 (1-PROV) (red), or vehicle (black) for 6 weeks (10 mg/Kg, IP.). (FIG. 9D) Quantification of human leukocytes (hCD45+), macrophages (hCD14+), T-lymphocytes (hCD3+), and B-lymphocytes (hCD19+) in HIV-infected humanized mice daily administered with MS882 (31), MS796 (1-PROV), or vehicle demonstrating that MS882 (31) selectively decreased populations of CD14+ macrophages. Data are mean±S.E. Comparisons between group of Vehicle and MS882 (31) are shown as *, $p<0.05$ (One way ANOVA, Tukey post-hoc);

FIG. 10 demonstrates that inhibition of nSMase2 decreased elevations of multiple ceramides. Quantifications of multiple ceramides in plasma from uninfected humanized mice, HIV-infected humanized mice administered MS882 (31) (10 mg/Kg) or vehicle for 6 weeks. Data are mean±S.D of n=4-6 per group. *=$p<0.05$; =$p<0.01$; *=$p<0.001$ compared to uninfected humanized mice #=$p<0.05$; ##=$p<0.01$ compared to HIV-infected mice administered vehicle. One-Way ANOVA with Tukey post-hoc comparisons;

FIG. 11A, FIG. 11B, FIG. 11C, FIG. 11D, FIG. 11E, FIG. 11F, FIG. 11G, FIG. 11H, FIG. 11I, FIG. 11J, FIG. 11K, and FIG. 11L show that the presently disclosed NSMase2 inhibitors do not have aberrant effects in animal health, behaviors, and clinical chemistry. (FIG. 11A) Weight of HIV infected humanized mice daily administered vehicle, MS882 (31) or MS796 (1-PROV), were weekly measured and presented as % changes based on weight of beginning of MS882 (31) administrations. (FIGS. 11A-11D) Quantification behavioral abnormalities combined with autonomic nervous system including ptosis, exophthalmus, miosis, mydriasis, corneal reflex loss, pinna reflex loss, piloerection, hyperventilation, writhing, tail erection, lacrimation, salivation, and vasodilation; somatomotor disturbances including hyperlocomotion, convulsion, arching, tremor, spraddle, leg weakness, escape loss, placing loss, grasping loss, righting loss, catalepsy, and tail pinch reflex; and grip strength in mice daily administered MS882 (31), MS796 (1-PROV), or vehicle at 11 weeks of infection (6 weeks of treatment). Each category was evaluated using a rating scale from 0 to 2 with 0=robust effect, 1=modest effects, 2=no effect. (FIG. 11E-11L) Quantification of enzyme activities or levels of indicators for liver or kidney dysfunctions. Alkaline phosphatase, ALP; Alanine aminotransferase, ALT; Aspartate aminotransferase, AST; Albumin, ALB; Glucose, GLU; Creatin, CREATIN; Blood urea nitrogen, BUN; Calcium, CA. Data are mean±S.D (n=4-6);

FIG. 12A, FIG. 12B, FIG. 12C, FIG. 12D, FIG. 12E, FIG. 12F, and FIG. 12G demonstrate that inhibition of nSMase2 decreased HIV RNAs and HIV+ macrophages in humanized mice. (FIG. 12A) Quantitative analysis of HIV RNAs in the tissues from the mice daily administered MS882 (31), MS796 (1-PROV), or vehicle for 6 weeks (n=3-6 in each group). RNAs from spleen, lung, liver, and brain (hippocampus) were extracted and analyzed by qRT-PCR for HIV1-p24. (FIG. 12A-FIG. 12E) Representative images (left) and quantification (right) of HIV+(p24+, red) macrophages (hCD14+, green) in spleen (FIG. 12B), lung (FIG. 12C), liver (FIG. 12D), and brain (FIG. 12E) from the mice daily administered MS882 (31), MS796 (1-PROV), or vehicle for 6 weeks (n=3-6 in each group). Total number of double immunopositive cells in tissue sections were measured, and presented as averaged number of double immunopositive cells/cm$^2$. (FIG. 12F) Experimental schemes of adoptive transfer. Splenocytes from HIV-infected humanized mice daily administered MS882 (31), antiretrovirals (ARVs, combinations of azidothymidine, lamivudine, and indinavir, I.P., 45 mg/kg/day for each drug) for 10-weeks were transferred to uninfected humanized mice, and sacrificed at 6-weeks after transfer. (FIG. 12G) Plasma viral loads in adoptively transferred mice at 6-weeks of transfer. RNAs were extracted from plasma and viral load was calculated by quantitative RT-PCR (n=3-4/group). Data are mean±S.D. *=p<0.05, **, =p<0.01 compared to uninfected (FIG. 12A) or HIV+ (FIG. 12B-FIG. 12E); #, p<0.05 compared to HIV+. One-way ANOVA with Tukey. Scale bar 20 μm; and FIG. 13A, FIG. 13B, and FIG. 13C demonstrate that NSMase2 inhibitors eradicated viral reservoirs in humanized mice. (FIG. 13A) Experimental schemes of administrations of MS882 (31) for 10 weeks, withdrawal for 8 weeks, and activation of viral reservoirs by latency reversing agents (LRAs) for 2 weeks. (FIG. 13B) Quantitative analysis of plasma viremia from the mice daily administered MS882 (31) (I.P., 10 mg/Kg, blue triangle, n=7), antiretrovirals (combination of azidothymidine, lamivudine, and indinavir, I.P., 45 mg/kg/day for each drug, green square, n=7), or vehicle (block circle, n=7) for 10 weeks, followed by withdrawal for 8 weeks, and administered LRAs (vorinostat, 100 mg/Kg, I.P.; iBet, 20 mg/Kg, I.P.) for 2 weeks. (FIG. 13C) Plasma viremia of the individual mouse administered MS882 (31) (n=7), followed by withdrawal, and LRAs.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Inhibition of nSMase for the Treatment of Human Immunodeficiency Virus Infection Small molecule inhibitors of neutral sphingomyelinase 2 (nSMase2) have been described in international PCT patent application no. PCT/US18/12699 for Small Molecule Inhibitors of Neutral Sphingomyelinase 2 (nSMase2) for the Treatment of Neurodegenerative Diseases, to Slusher et al., filed Jan. 5, 2018, which is incorporated by reference in its entirety. The presently disclosed subject matter demonstrates the utility of those inhibitors to block replication of the Human Immunodeficiency Virus (HIV). Maturation of HIV requires budding of the virus from cellular membranes. Inhibitors of nSMase interfere with the HIV life cycle by preventing viral assembly and budding. Such activity for nSMase2 inhibition has not been reported previously.

Accordingly, in some embodiments, the presently disclosed subject matter provides a method for treating a Human Immunodeficiency Virus (HIV) infection, the method comprising administering to a subject in need of treatment thereof an effective amount of an nSMase2 inhibitor of formula (I):

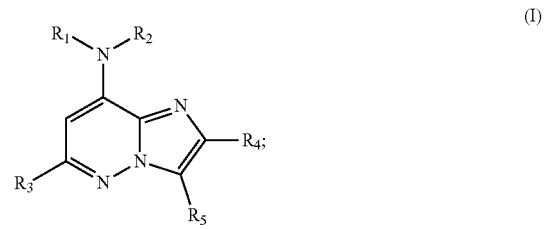

wherein:
 $R_1$ and $R_2$ are each independently selected from substituted or unsubstituted alkyl or together with the nitrogen atom to which they are bound form a substituted or unsubstituted 5- or 6-membered heterocyclic ring;
 $R_3$ is selected from the group consisting of H, substituted or unsubstituted alkyl, substituted or unsubstituted alkoxyl, substituted or unsubstituted thioalkyl, substituted or unsubstituted aryl, and halogen;
 $R_4$ is selected from the group consisting of H, substituted or unsubstituted alkyl, and substituted or unsubstituted aryl;
 $R_5$ is selected from the group consisting of H, halogen, substituted or unsubstituted alkyl, substituted or unsubstituted aryl, substituted or unsubstituted heteroaryl, and a substituted or unsubstituted multicyclic aryl or multicyclic heteroaryl ring;
 under the proviso that if $R_1$ and $R_2$ together with the nitrogen atom to which they are bound are pyridinyl or morpholinyl, then $R_5$ cannot be H, halogen, or substituted or unsubstituted heteroaryl; and pharmaceutically acceptable salts thereof.

One of ordinary skill in the art upon review of the presently disclosed subject matter would appreciate that compounds disclosed in U.S. patent application publication no. US20120220581A1 for Imidazo[1,2-b]pyridazine Derivatives and their use as PDE10 Inhibitors, to Pastor-Fernández, published Aug. 30, 2012, are not included in the presently disclosed compounds.

In particular embodiments, the substituted alkyl or unsubstituted alkyl represented by $R_1$, $R_2$, $R_3$, $R_4$, and $R_5$ of formula (I) can be a $C_1$, $C_2$, $C_3$, $C_4$, $C_5$, $C_6$, $C_7$, or $C_8$ linear or branched alkyl, in some embodiments, $C_{1-4}$ substituted or unsubstituted alkyl, in some embodiments, $C_{1-6}$ substituted or unsubstituted alkyl, in some embodiments, $C_{1-8}$ alkyl substituted or unsubstituted alkyl, including, but not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, and the like, each of which can include one or more substituents. Representative substituent groups include, but are not limited to, alkyl, substituted alkyl, halogen, aryl, substituted aryl, alkoxyl, hydroxyl, nitro, amino, alkylamino, dialkylamino, sulfate, cyano, mercapto, and alkylthio.

In further embodiments, the 5- to 6-membered heterocyclic ring formed from $R_1$ and $R_2$ together with the nitrogen to which they are bound includes, but is not limited to, pyrrolidinyl, imidazolidinyl, imidazolinyl, pyrazolidinyl, pyrazolinyl, piperidinyl, piperazinyl, indolinyl, 3-pyrrolinyl, morpholinyl, and the like.

In certain embodiments, the substituted or unsubstituted alkyl, substituted or unsubstituted aryl, substituted or unsubstituted heteroaryl, and a substituted or unsubstituted multicyclic aryl or multicyclic heteroaryl ring represented by $R_5$ of formula (I) includes phenyl, thiophen-2-yl, furanyl, thiazolyl, pyridinyl, indolyl, benzo[d][1,3]dioxolyl, and the like.

In some embodiments, the compound of formula (I) is:

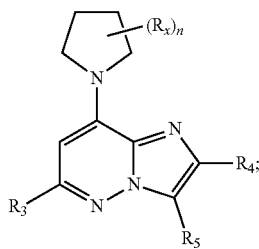

wherein:
n is an integer selected from the group consisting of 0, 1, 2, 3, 4, 5, 6, 7, and 8;

$R_x$ is selected from the group consisting of halogen, hydroxyl, alkoxyl, thioalkyl, cyano, amino, —$N_3$, substituted or unsubstituted aryl, substituted or unsubstituted cycloheteroalkyl, substituted or unsubstituted heteroaryl, —X—(C=O)—$C_{1-6}$ alkyl, wherein X is O or S, and —$NR_6R_7$, wherein $R_6$ is selected from the group consisting of H or substituted or unsubstituted $C_{1-6}$ alkyl; and $R_7$ is selected from the group consisting of —C(=O)—$(CR_yR_z)_m$—$R_8$, —C(=O)—$(CR_yR_z)_m$—O—$R_8$, —C(=O)—O—$(CR_yR_z)_m$—$R_8$, and —S(=O)$_2$—$R_9$, wherein each m is an integer selected from the group consisting of 0, 1, 2, 3, 4, 5, and 6, $R_y$ and $R_z$ are each independently H, alkoxyl, or halogen, $R_8$ and $R_9$ are each independently selected from the group consisting of substituted or unsubstituted alkyl, —$CF_3$, substituted or unsubstituted cycloalkyl, substituted or unsubstituted aryl, substituted or unsubstituted cycloheteroaryl, substituted or unsubstituted multicyclic aryl or heteroaryl ring, and $NR_{10}R_{11}$, wherein $R_{10}$ and $R_{11}$ are each independently selected from the group consisting of H, substituted or unsubstituted $C_{1-6}$ alkyl, and substituted or unsubstituted aryl.

In particular embodiments, the compound of formula (I) is:

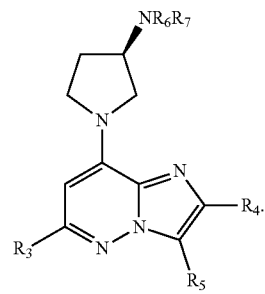

In yet more particular embodiments, the compound of formula (I) is:

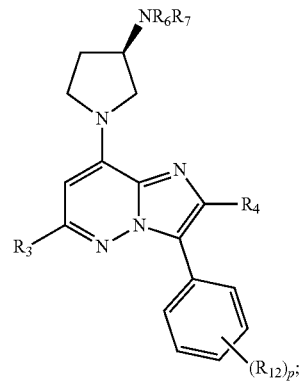

wherein:
p is an integer selected from the group consisting of 0, 1, 2, 3, 4, and 5;

each $R_{12}$ is independently selected from the group consisting of substituted or unsubstituted alkyl, hydroxyl, alkoxyl, halogen, cyano, amino, —$CF_3$, —O—$CF_3$, substituted or unsubstituted cycloheteroaklyl, —$NR_{13}$(C=O)$R_{14}$, —S(=O)$_2$—$R_{15}$, —S(=O)$_2$—$NR_{15}R_{16}$, —$SR_{16}$, —C(=O)—$R_{17}$, —C(=O)—O—$R_{18}$, and —C(=O)—$NR_{19}R_{20}$, wherein $R_{13}$ is selected from the group consisting of H or substituted or unsubstituted $C_{1-6}$ alkyl, $R_{14}$ is substituted or unsubstituted $C_{1-6}$ alkyl or —O—$R_{21}$, and $R_{15}$, $R_{16}$, $R_{17}$, $R_{18}$, $R_{19}$, $R_{20}$, $R_{21}$ are each independently H or substituted or unsubstituted $C_{1-6}$ alkyl.

In certain embodiments, $R_6$ is H and $R_7$ is —C(=O)—$(CR_yR_z)_m$—$R_8$, wherein m is 0 and $R_8$ is $C_{1-6}$ alkyl. In particular embodiments, the compound of formula (I) is selected from the group consisting of:

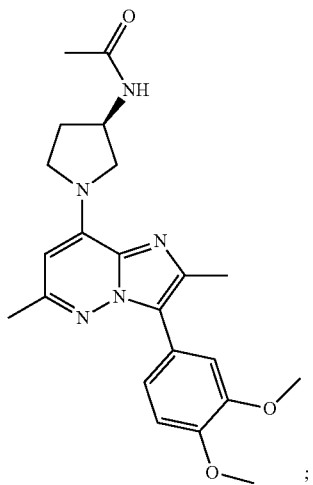
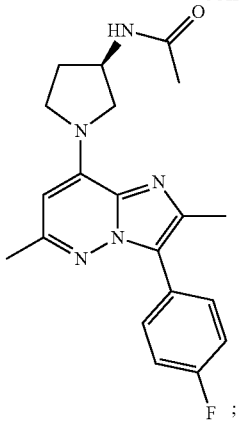
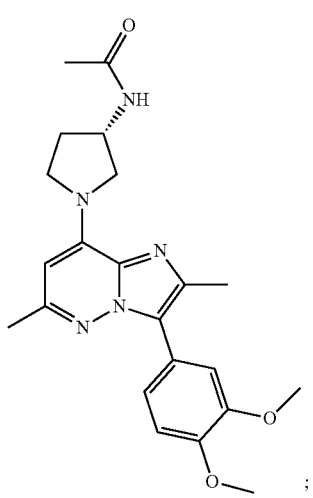
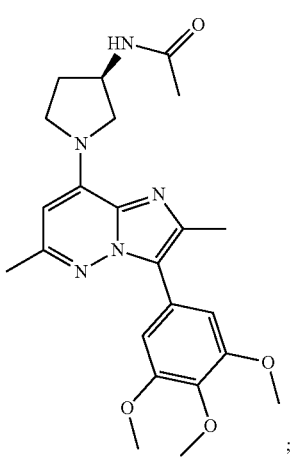
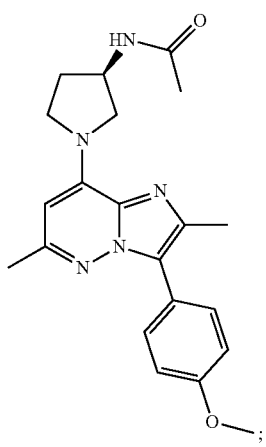

-continued
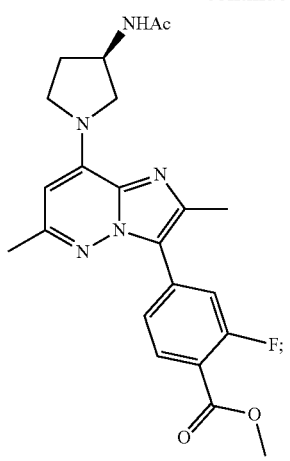
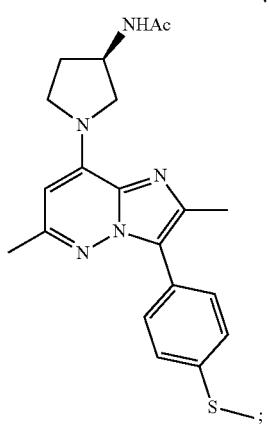
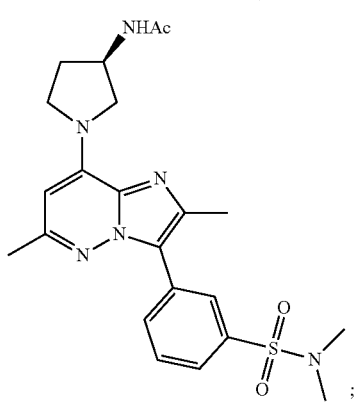
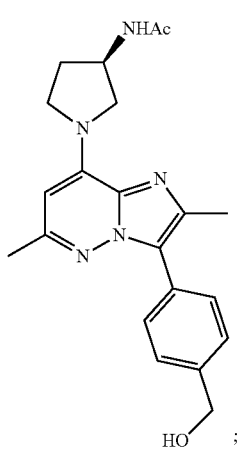
-continued
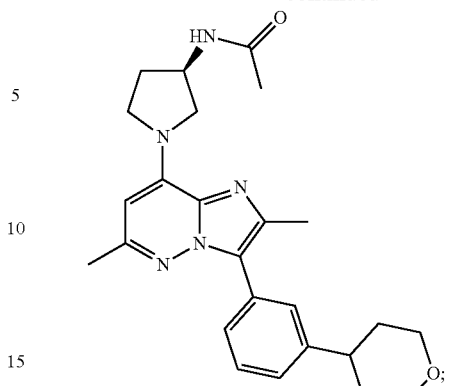
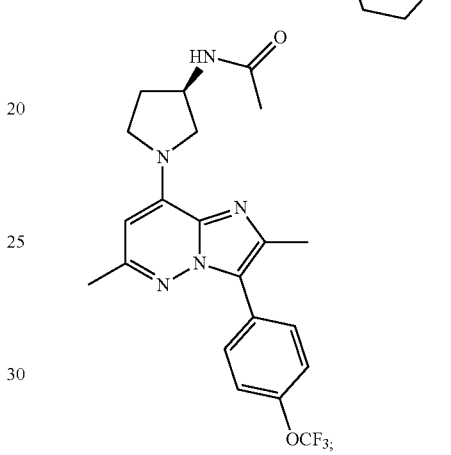
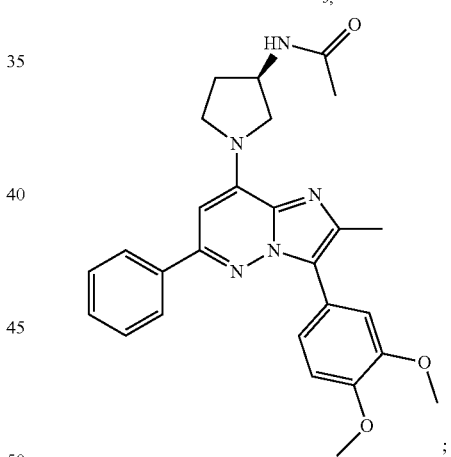
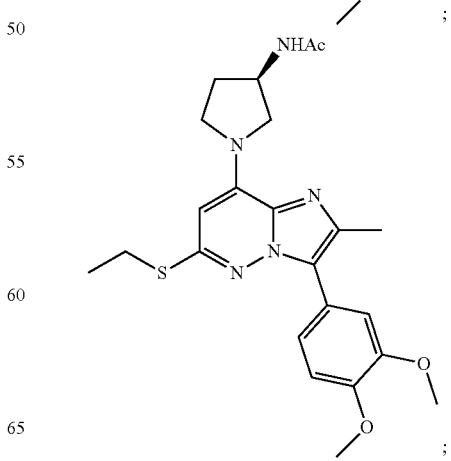

-continued
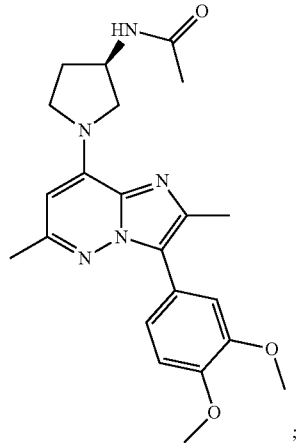
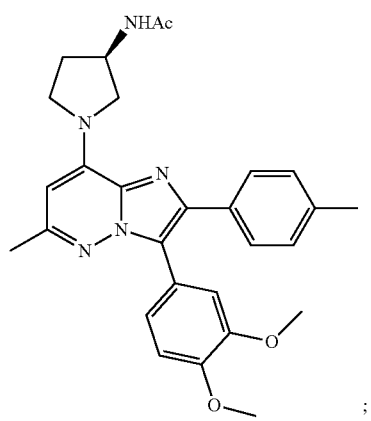
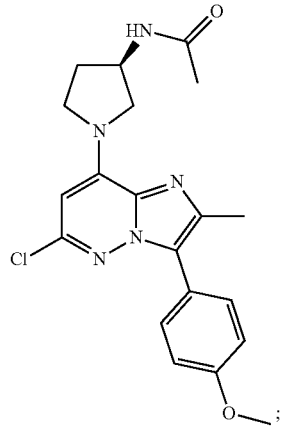
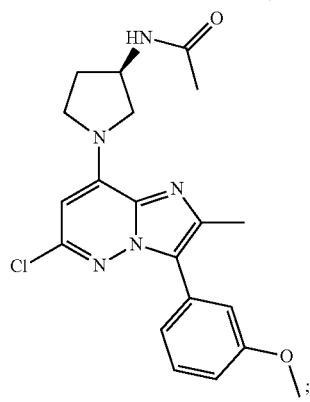
-continued
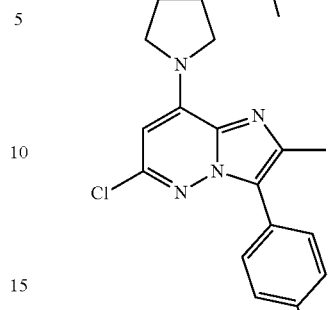
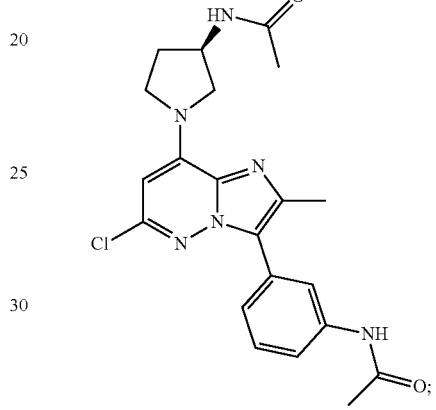
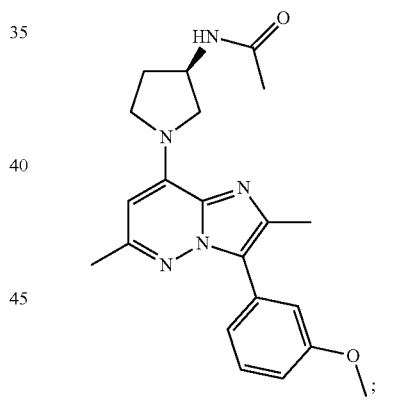
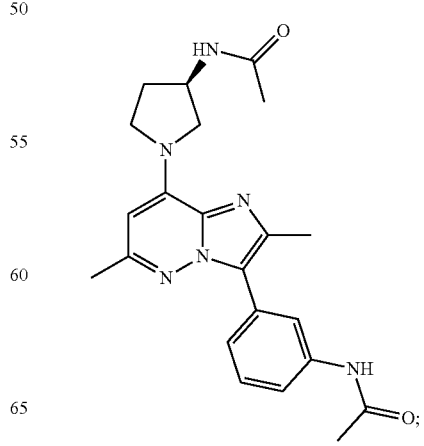

17
-continued

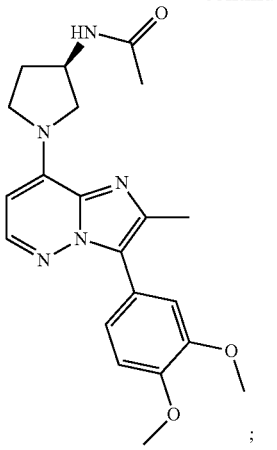

;

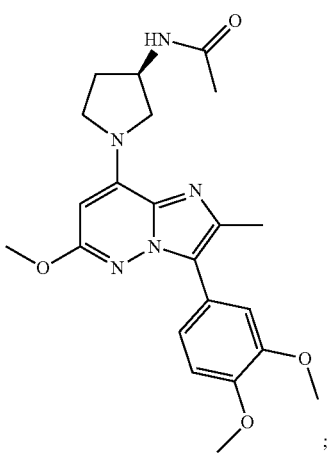

;

18
-continued

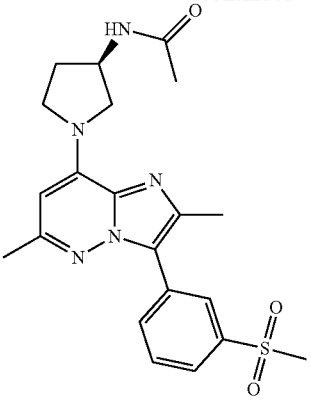

; and

OH.

In certain embodiments, $R_6$ is H and $R_7$ is selected from the group consisting of —C(=O)—(CR$_y$R$_z$)$_m$—R$_8$, —C(=O)—(CR$_y$R$_z$)$_m$—O—R$_8$, —C(=O)—O—(CR$_y$R$_z$)$_m$—R$_8$, wherein each m is an integer selected from the group consisting of 0, 1, 2, 3, 4, 5, and 6, $R_y$ and $R_z$ are each independently H, alkoxyl, or halogen, $R_8$ is selected from the group consisting of substituted or unsubstituted alkyl, —CF$_3$, substituted or unsubstituted cycloalkyl, substituted or unsubstituted aryl, substituted or unsubstituted cycloheteroaryl, substituted or unsubstituted multicyclic aryl or heteroaryl ring, and NR$_{10}$R$_{11}$, wherein R$_{10}$ and R$_{11}$ are each independently selected from the group consisting of H, substituted or unsubstituted C$_{1-6}$ alkyl, and substituted or unsubstituted aryl. In particular embodiments, the compound of formula (I) is selected from the group consisting of:

19
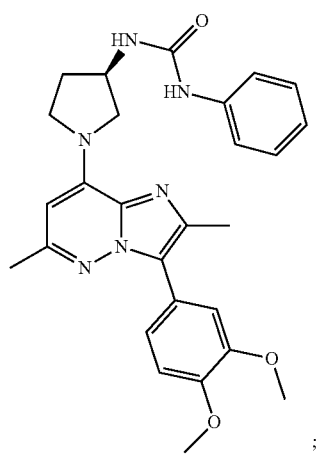
;
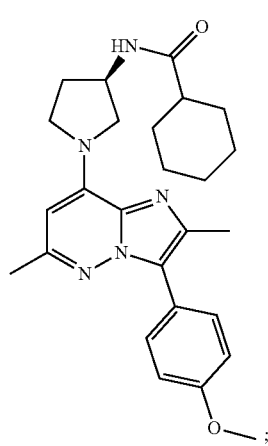
;
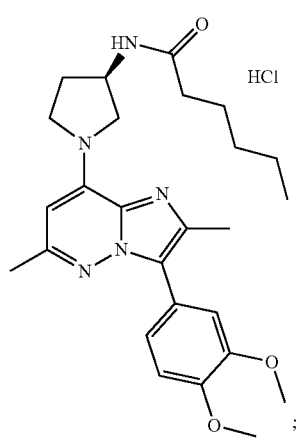 HCl
;
20
-continued
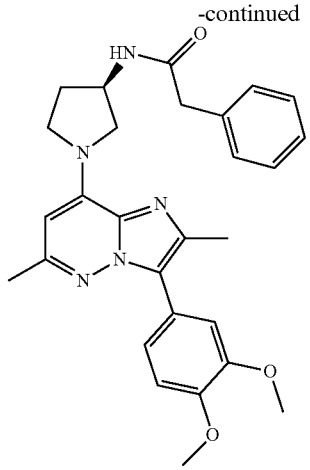
;
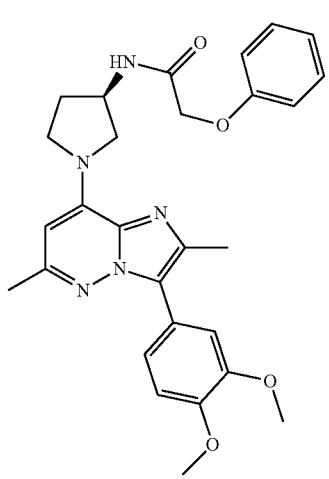
;
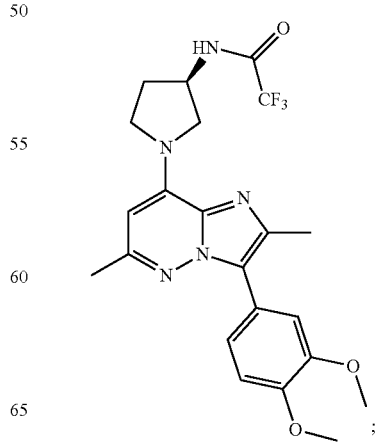
;

21
-continued
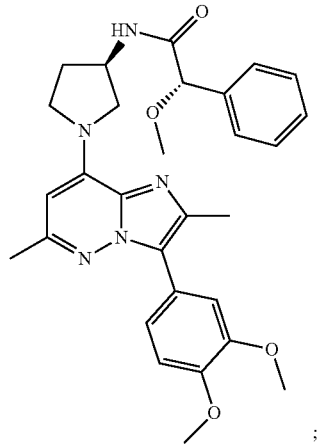
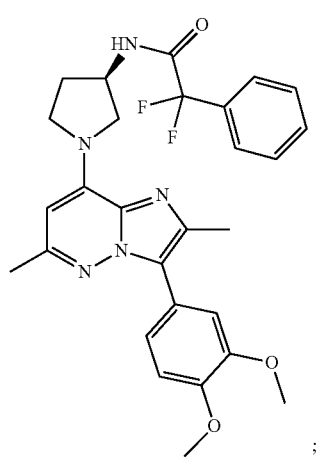
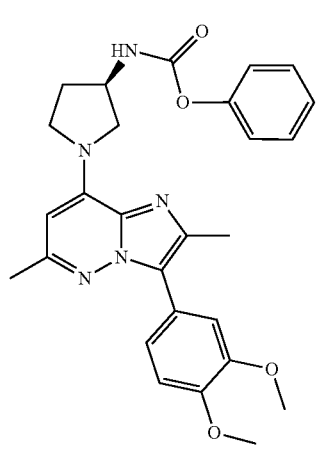
22
-continued
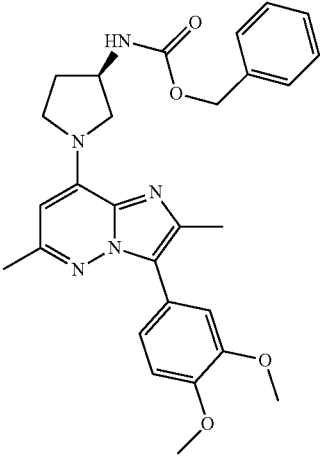
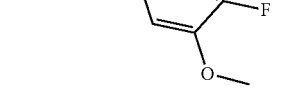
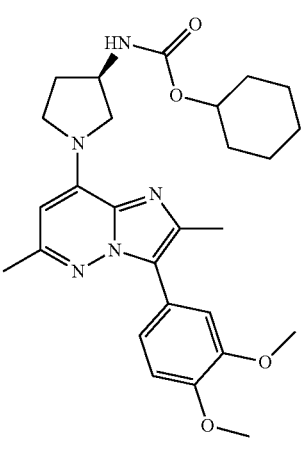

-continued
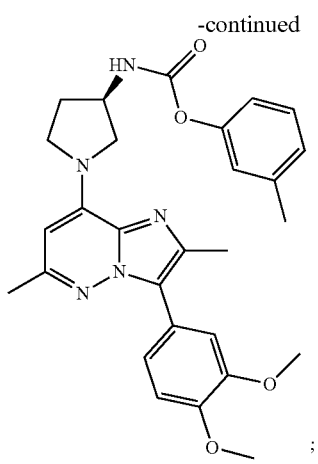
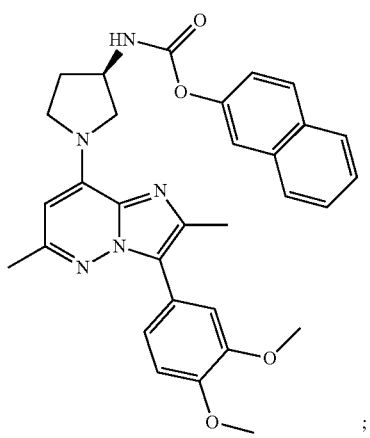
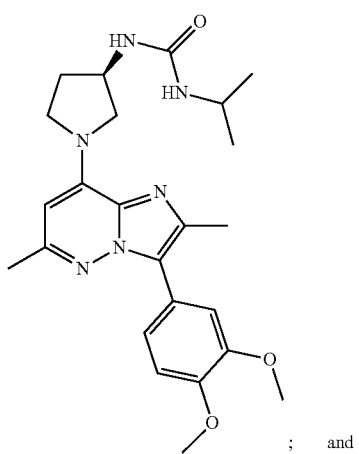
and
-continued
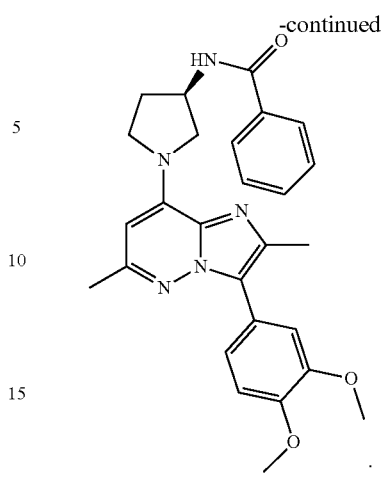
In certain embodiments, $R_6$ is H and $R_7$ is —S(=O)$_2$—$R_9$. In particular embodiments, the compound of formula (I) is selected from the group consisting of:
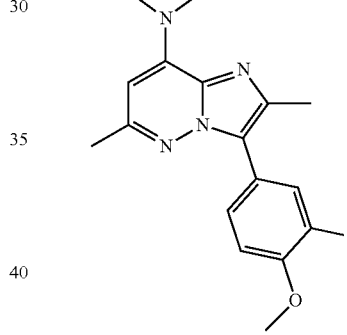
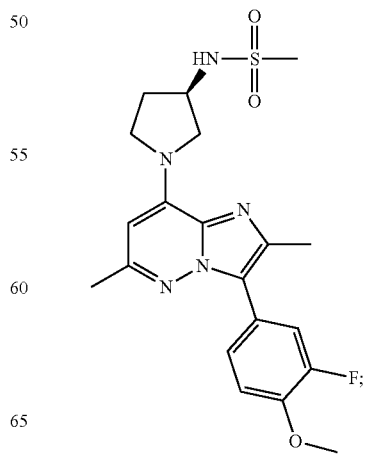

25
-continued
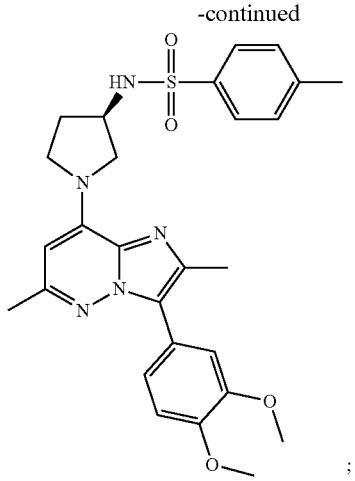
;
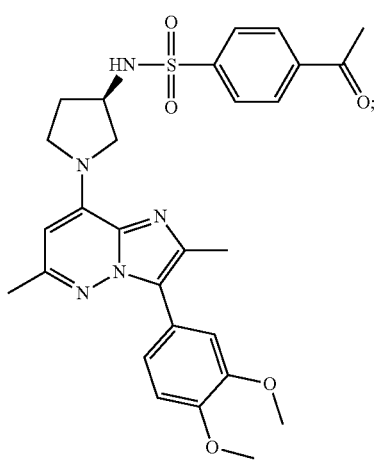
;
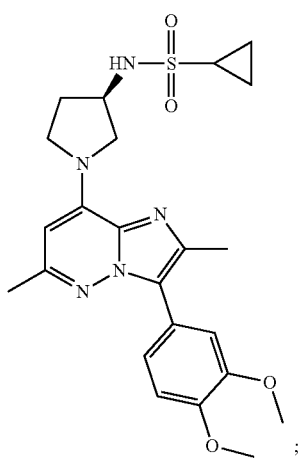
;
26
-continued
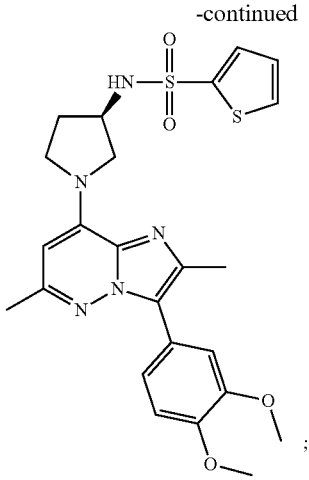
;
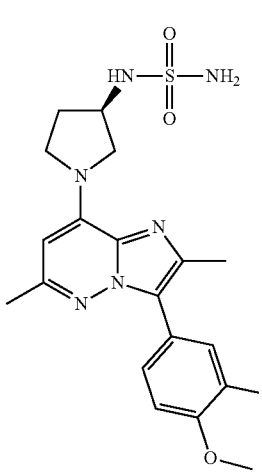
;
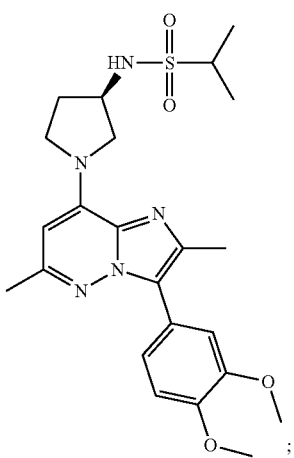
;

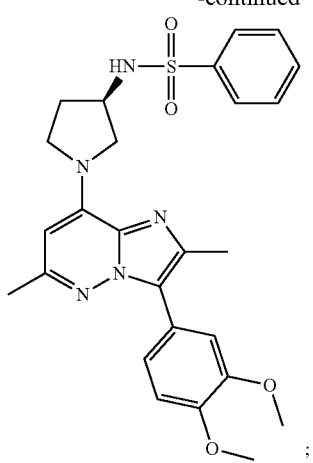
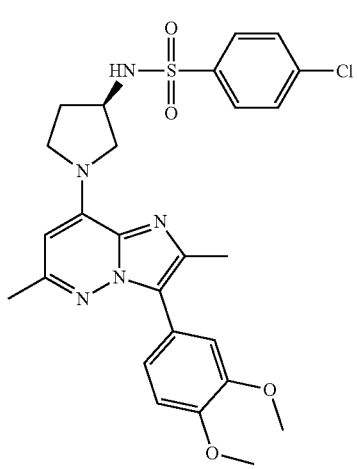
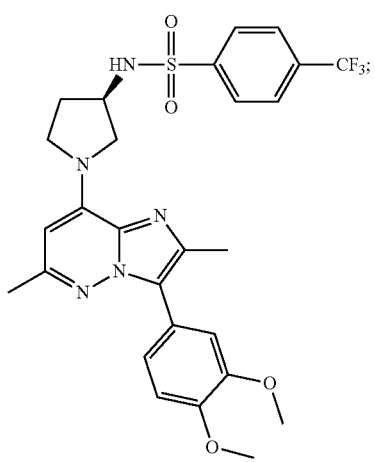
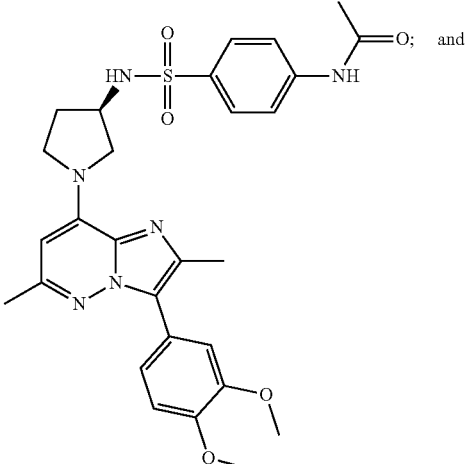
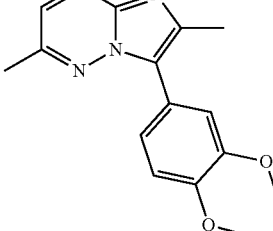
In certain embodiments, R$_5$ is selected from the group consisting of H, halogen, and substituted or unsubstituted alkyl. In particular embodiments, the compound of formula (I) is selected from the group consisting of:
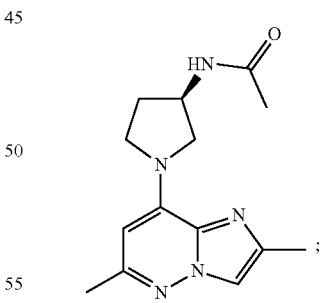
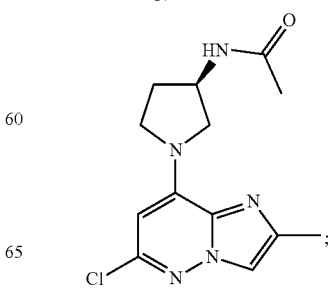

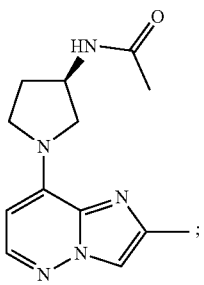

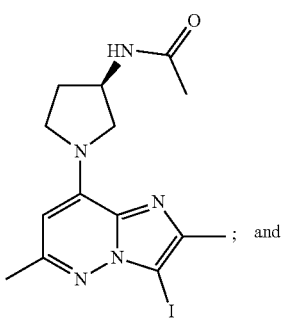; and

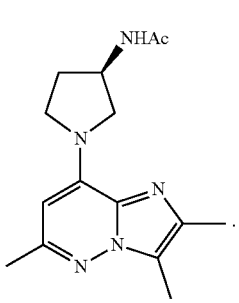

In certain embodiments, R₅ is a substituted or unsubstituted multicyclic aryl or multicyclic heteroaryl ring. In particular embodiments, the compound of formula (I) is selected from the group consisting of:

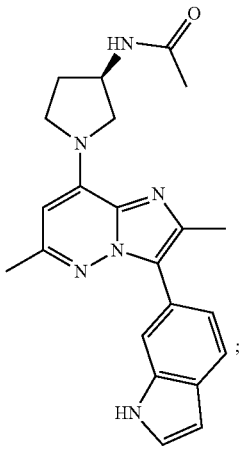;

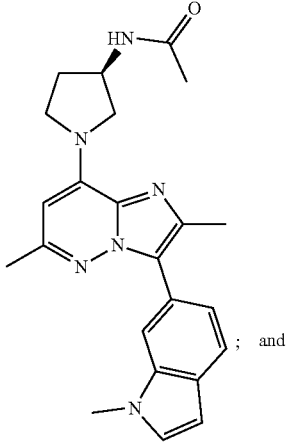; and

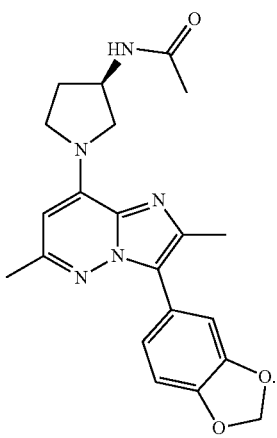

In certain embodiments, R₅ is a substituted or unsubstituted heteroaryl. In particular embodiments, the compound of formula (I) is selected from the group consisting of:

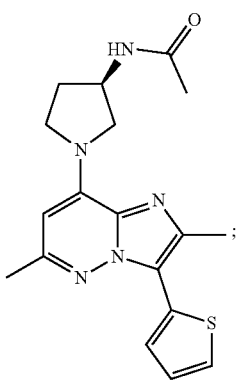;

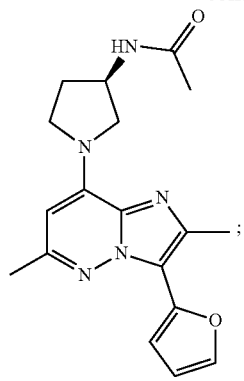

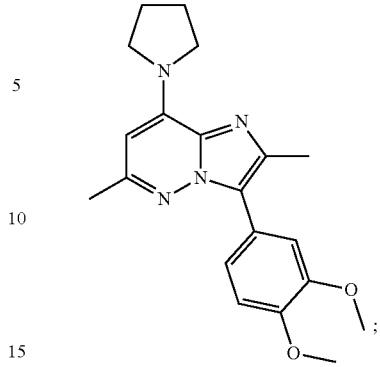

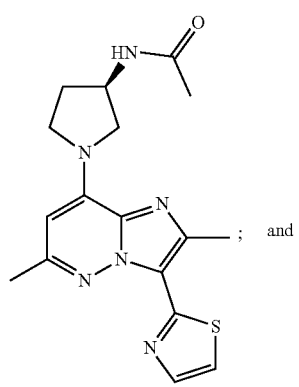

and

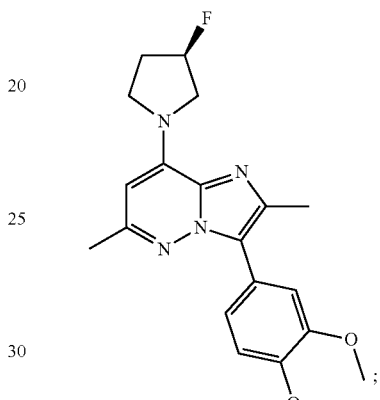

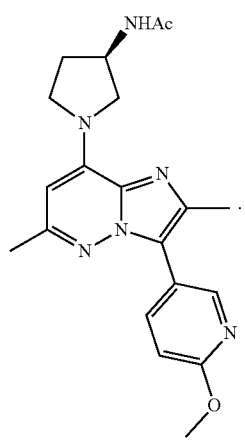

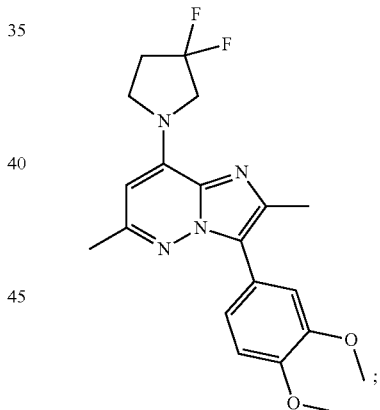

In certain embodiments, n is 0, 1, or 2 and $R_x$ is selected from the group consisting of halogen, hydroxyl, alkoxyl, thioalkyl, cyano, amino, —$N_3$, substituted or unsubstituted aryl, substituted or unsubstituted cycloheteroalkyl, substituted or unsubstituted heteroaryl, and —X—(C=O)—$C_{1-6}$ alkyl, wherein X is O or S. In particular embodiments, the compound of formula (I) is selected from the group consisting of:

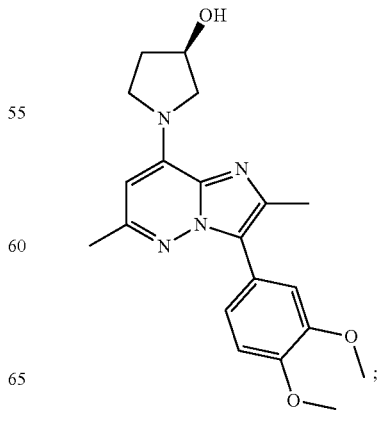

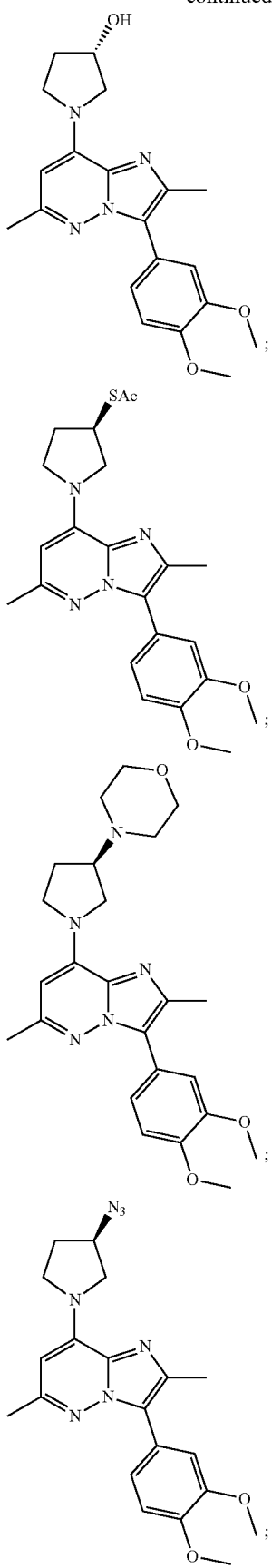
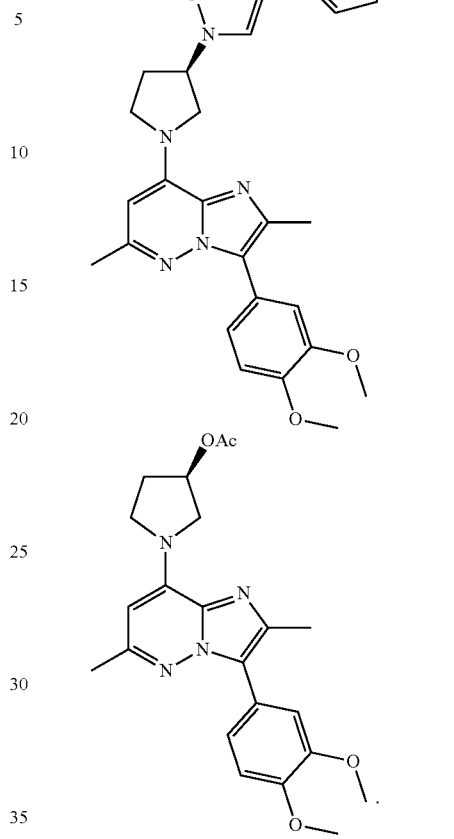
In certain embodiments, R$_1$ and R$_2$ together with the nitrogen atom to which they are bound form a substituted or unsubstituted 5- or 6-membered heterocyclic ring selected from the group consisting of:
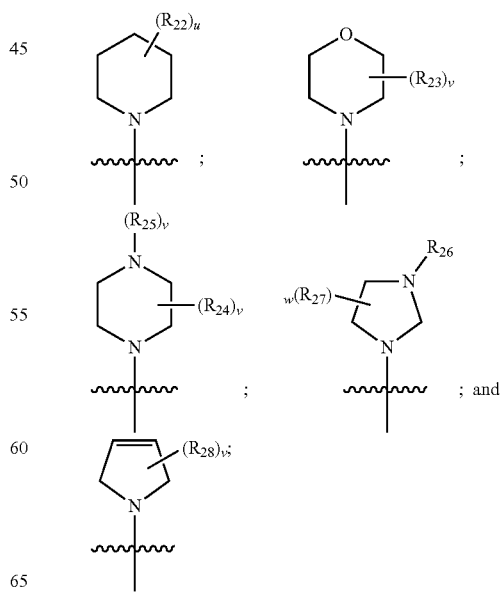

wherein:
- u is an integer selected from the group consisting of 0, 1, 2, 3, 4, and 5;
- each v is independently an integer selected from the group consisting of 0, 1, 2, 3, and 4;
- w is an integer selected from the group consisting of 0, 1, 2, and 3; and
- $R_{22}$, $R_{23}$, $R_{24}$, $R_{25}$, $R_{26}$, $R_{27}$, and $R_{28}$ are each independently selected from the group consisting of H, —(C=O)—$R_{29}$, —(C=O)—O—$R_{30}$, —S(=O)$_2$—$R_{31}$, and —N$R_{32}$—C(=O)—$R_{33}$, wherein $R_{29}$, $R_{30}$, $R_{31}$, $R_{32}$, and $R_{33}$ are each independently selected from the group consisting of H, substituted or unsubstituted alkyl, and substituted or unsubstituted cycloalkyl. In particular embodiments, the compound of formula (I) is selected from the group consisting of:

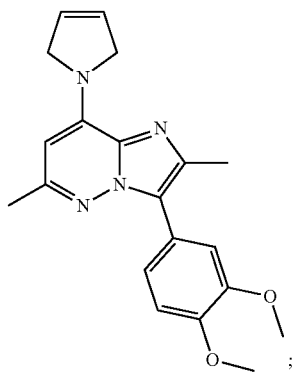

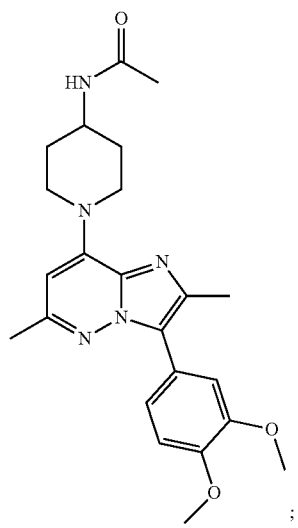

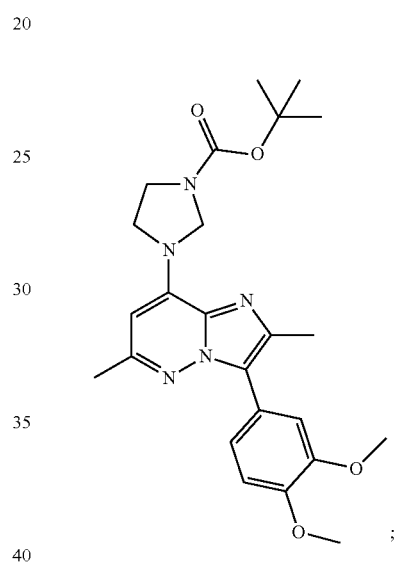

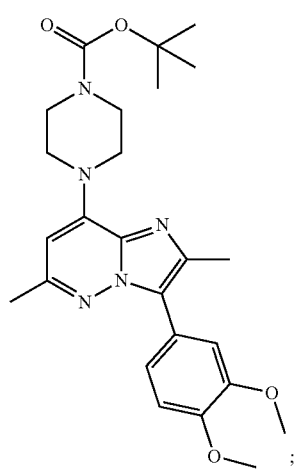

-continued
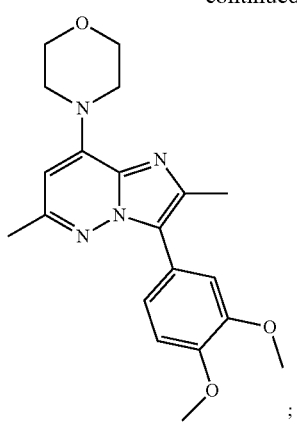
;
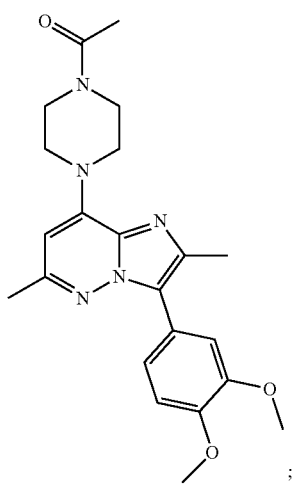
; and
-continued
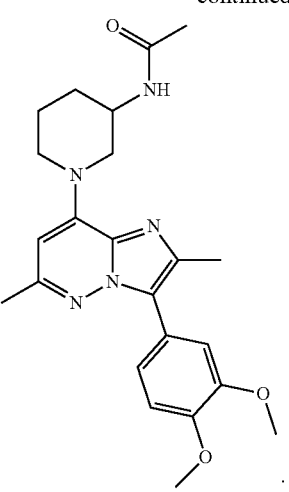
.
In certain embodiments, $R_1$ and $R_2$ are each independently selected from substituted or unsubstituted alkyl. In particular embodiments, the compound of formula (I) is:
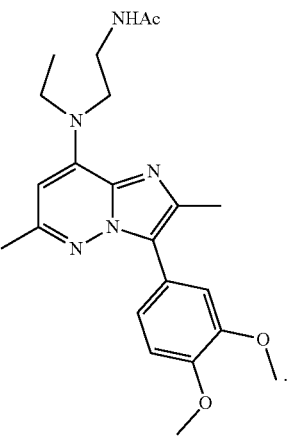
.
Representative compounds of formula (I) and their activities are summarized in Table 1A.

TABLE 1A

Representative Inhibitors of nSMase2 of Formula (I)

| Entry | Structure | IC$_{50}$ (μM) |
|---|---|---|
| 1 | 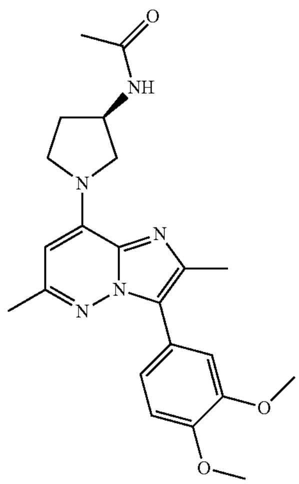 | 1 |
| 2 | 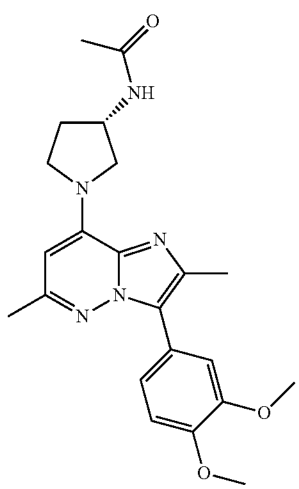 | 2 |
| 3 | 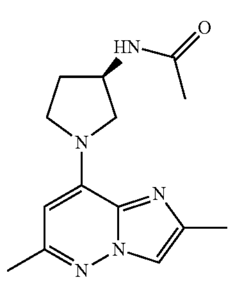 | 8 |
| 4 | | 1 |
| 5 | | 2 |
| 6 | | 1 |

TABLE 1A-continued

Representative Inhibitors of nSMase2 of Formula (I)

| Entry | Structure | IC$_{50}$ (μM) |
|---|---|---|
| 7 | (imidazo[1,2-b]pyridazine with 2,6-dimethyl, 8-(3-acetamidopyrrolidin-1-yl), 3-(3-fluoro-4-methoxyphenyl)) | 0.6 |
| 8 | (imidazo[1,2-b]pyridazine with 2,6-dimethyl, 8-(3-acetamidopyrrolidin-1-yl), 3-(2-fluoro-4-methoxycarbonylphenyl)) | 0.4 |
| 9 | (imidazo[1,2-b]pyridazine with 2,6-dimethyl, 8-(3-acetamidopyrrolidin-1-yl), 3-(4-methylthiophenyl)) | 0.2 |
| 10 | (imidazo[1,2-b]pyridazine with 2,6-dimethyl, 8-(3-acetamidopyrrolidin-1-yl), 3-(3-(N,N-dimethylsulfamoyl)phenyl)) | 0.5 |
| 11 | (imidazo[1,2-b]pyridazine with 2,6-dimethyl, 8-(3-acetamidopyrrolidin-1-yl), 3-(6-methoxypyridin-3-yl)) | 0.5 |
| 12 | (imidazo[1,2-b]pyridazine with 2,6-dimethyl, 8-(3-acetamidopyrrolidin-1-yl), 3-(4-(hydroxymethyl)phenyl)) | 0.4 |

TABLE 1A-continued
Representative Inhibitors of nSMase2 of Formula (I)
| Entry | Structure | IC$_{50}$ (μM) |
|---|---|---|
| 13 | 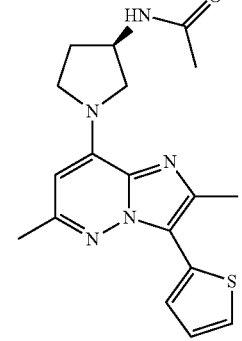 | 0.3 |
| 14 | 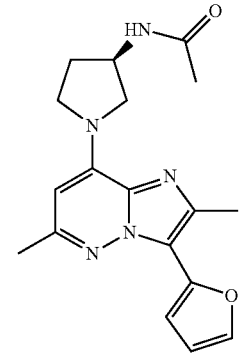 | 0.9 |
| 15 | 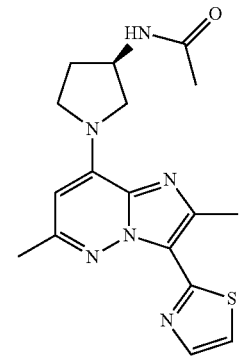 | 1 |
| 16 | 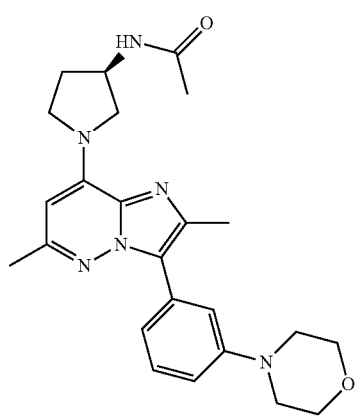 [SMILES: CC(=O)N[C@@H]1CCN(c2cc(C)nn3c(-c4cccc(N5CCOCC5)c4)c(C)nc23)C1] | 0.8 |
| 17 | 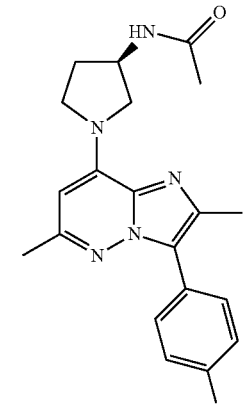 | 0.2 |
| 18 | 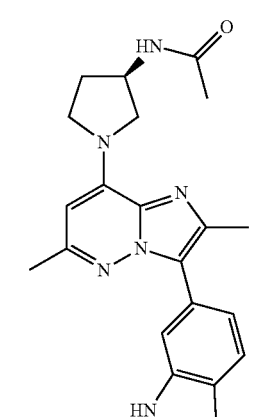 | 0.7 |
| 19 | 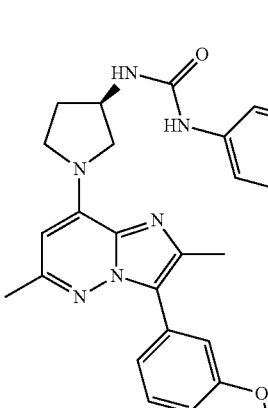 | 0.2 |

TABLE 1A-continued

Representative Inhibitors of nSMase2 of Formula (I)

| Entry | Structure | IC$_{50}$ (μM) |
|---|---|---|
| 20 | 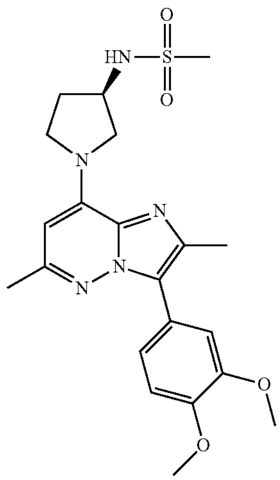 | 1 |
| 21 | 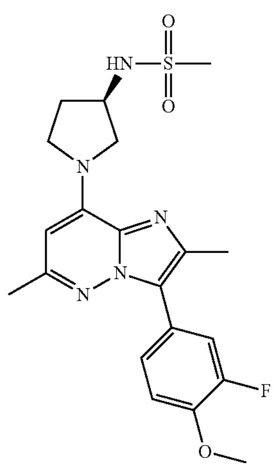 [SMILES: COc1ccc(-c2c(C)nc3c(N4CC[C@@H](NS(C)(=O)=O)C4)cc(C)nn23)cc1F] | 0.1 |
| 22 | 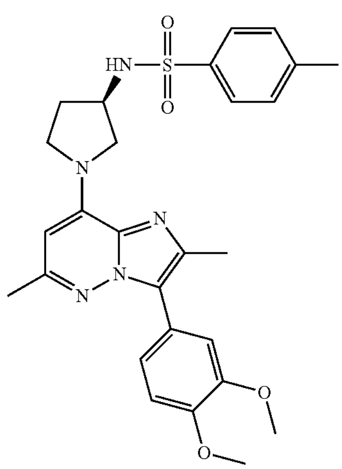 | 0.09 |
| 23 | | 0.2 |
| 24 | | 0.1 |
| 25 | | 0.1 |

TABLE 1A-continued
Representative Inhibitors of nSMase2 of Formula (I)
| Entry | Structure | IC$_{50}$ (μM) |
|---|---|---|
| 26 | 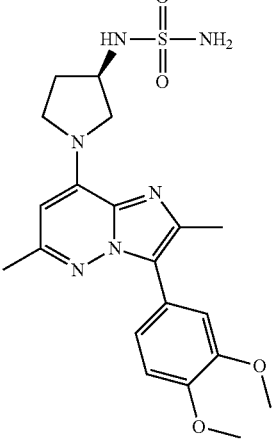 | 0.3 |
| 27 | 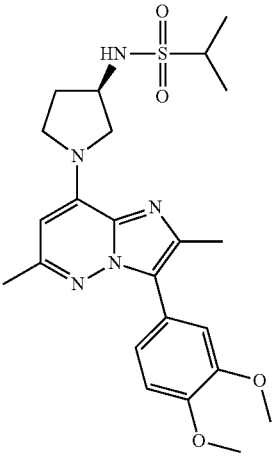 | 0.3 |
| 28 | 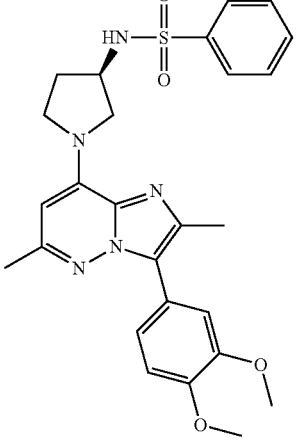 | 0.5 |
| 29 | 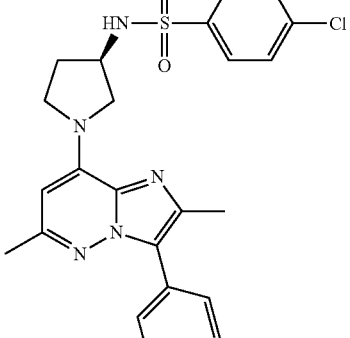 | 0.4 |
| 30 | 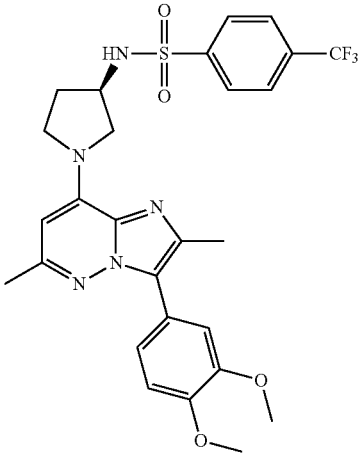 [SMILES: COc1ccc(-c2c(C)nc3c(N4CC[C@@H](NS(=O)(=O)c5ccc(C(F)(F)F)cc5)C4)cc(C)nn23)cc1OC] | 0.2 |
| 31 (MS822) | 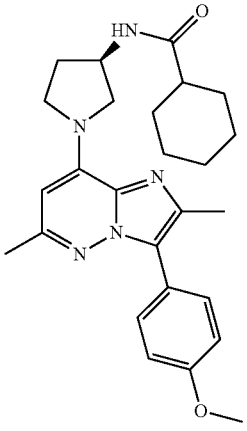 | 0.7 |

TABLE 1A-continued
Representative Inhibitors of nSMase2 of Formula (I)
| Entry | Structure | IC$_{50}$ (µM) |
|---|---|---|
| 32 | 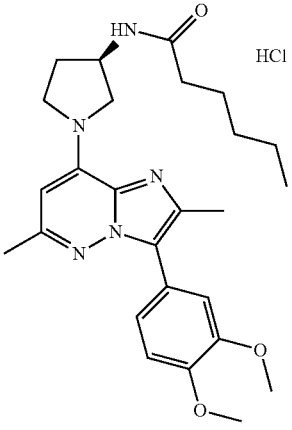 [SMILES: CCCCCC(=O)N[C@@H]1CCN(c2cc(C)nn3c(-c4ccc(OC)c(OC)c4)c(C)nc23)C1 ; Cl] HCl | 0.1 |
| 33 | 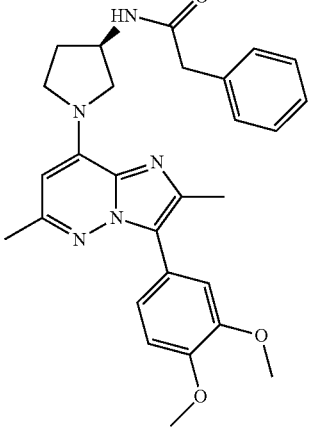 | 0.4 |
| 34 | 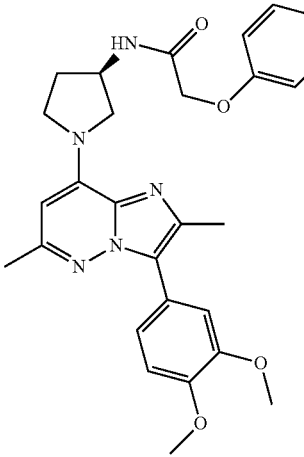 | 0.2 |
| 35 | 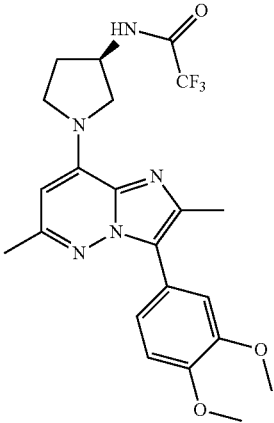 | 0.9 |
| 36 | 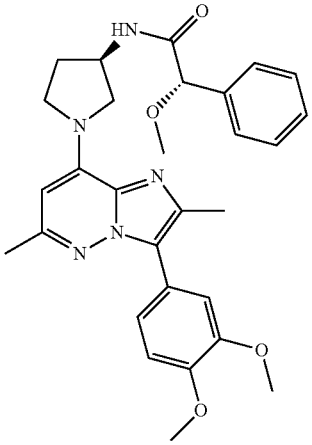 [SMILES: COc1ccc(-c2c(C)nc3c(N4CC[C@@H](NC(=O)[C@@H](OC)c5ccccc5)C4)cc(C)nn23)cc1OC] | 0.4 |
| 37 | 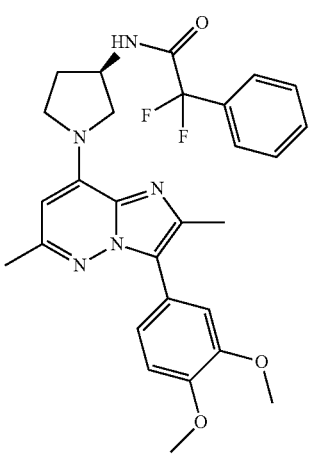 [SMILES: COc1ccc(-c2c(C)nc3c(N4CC[C@@H](NC(=O)C(F)(F)c5ccccc5)C4)cc(C)nn23)cc1OC] | 0.1 |

TABLE 1A-continued
Representative Inhibitors of nSMase2 of Formula (I)
| Entry | Structure | IC$_{50}$ (μM) |
|---|---|---|
| 38 | 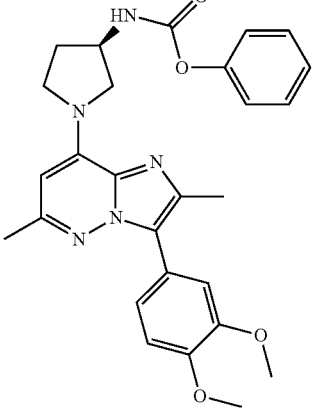 | 0.3 |
| 39 | 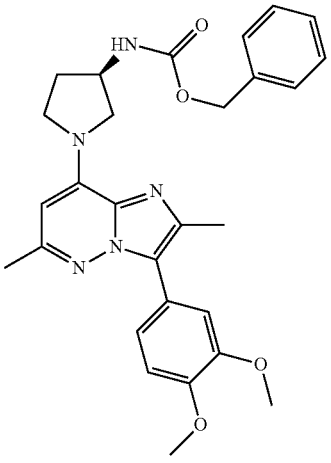 [SMILES: COc1ccc(-c2c(C)nc3c(N4CC[C@@H](NC(=O)OCc5ccccc5)C4)cc(C)nn23)cc1OC] | 0.3 |
| 40 | 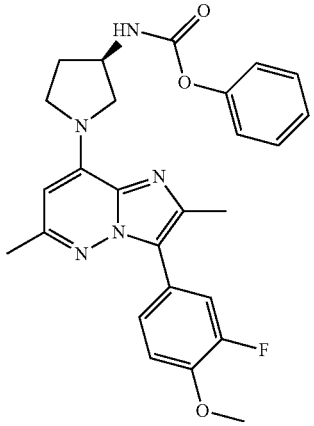 [SMILES: COc1ccc(-c2c(C)nc3c(N4CC[C@@H](NC(=O)Oc5ccccc5)C4)cc(C)nn23)cc1F] | 0.3 |
| 41 | 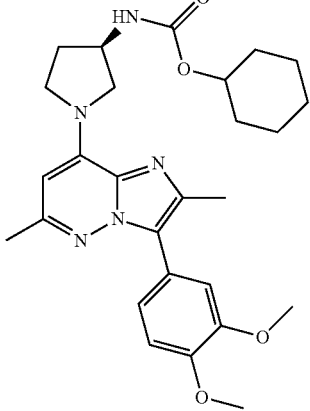 | 0.3 |
| 42 | 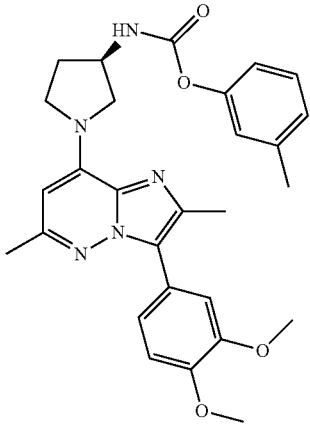 [SMILES: COc1ccc(-c2c(C)nc3c(N4CC[C@@H](NC(=O)Oc5cccc(C)c5)C4)cc(C)nn23)cc1OC] | 0.2 |
| 43 | 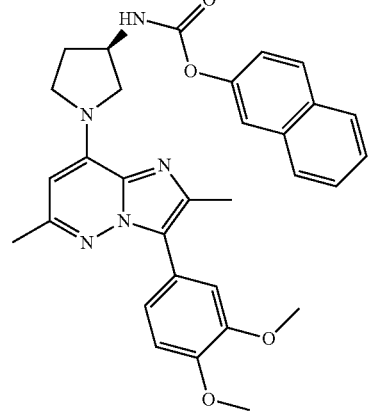 | 0.3 |

TABLE 1A-continued
Representative Inhibitors of nSMase2 of Formula (I)
| Entry | Structure | IC$_{50}$ (μM) |
|---|---|---|
| 44 | 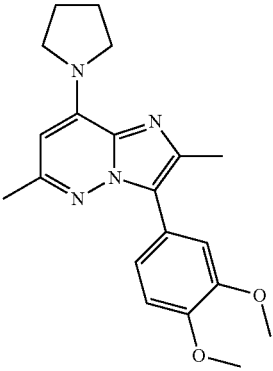 | 0.05 |
| 45 | 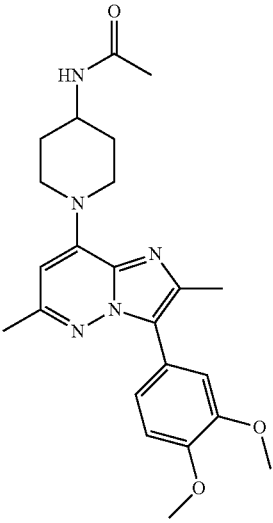 | 1 |
| 46 | 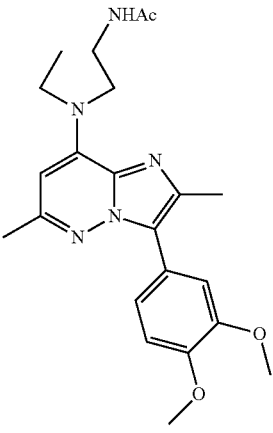 | 5 |
| 47 | 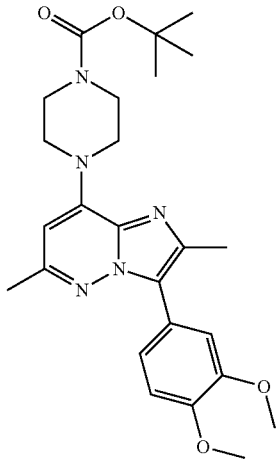 | 2 |
| 48 | 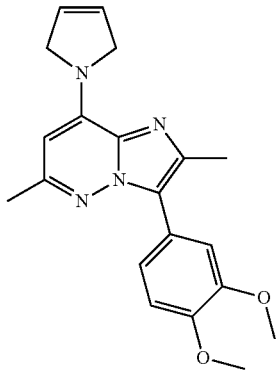 | 1 |
| 49 | 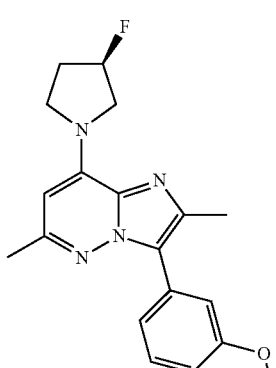 | 0.7 |

TABLE 1A-continued

Representative Inhibitors of nSMase2 of Formula (I)

| Entry | Structure | IC$_{50}$ (µM) |
|---|---|---|
| 50 | 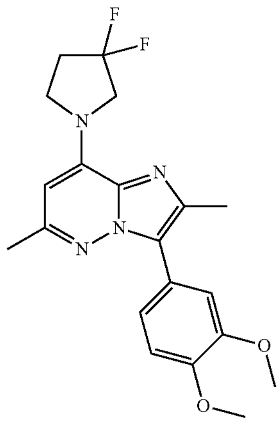 | 1 |
| 51 | 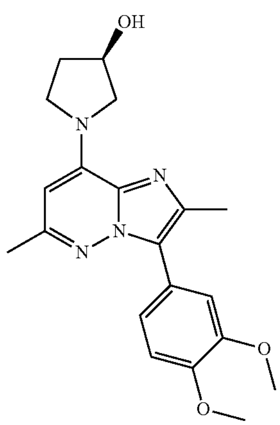 | 0.6 |
| 52 | 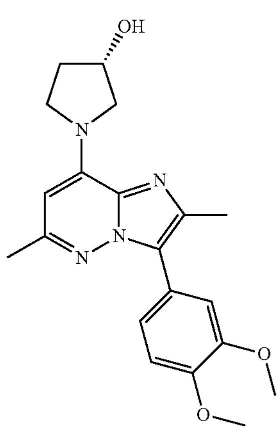 | 0.5 |
| 53 | | 0.9 |
| 54 | | 0.7 |
| 55 | | 1 |

TABLE 1A-continued

Representative Inhibitors of nSMase2 of Formula (I)

| Entry | Structure | IC$_{50}$ (μM) |
|---|---|---|
| 56 | (3,4-dimethoxyphenyl)-imidazo[1,2-b]pyridazine with pyrrolidine bearing SAc | 0.3 |
| 57 | (3,4-dimethoxyphenyl)-imidazo[1,2-b]pyridazine with pyrrolidine bearing morpholine | 0.7 |
| 58 | (3,4-dimethoxyphenyl)-imidazo[1,2-b]pyridazine with pyrrolidine bearing N$_3$ | 0.7 |
| 59 | (3,4-dimethoxyphenyl)-imidazo[1,2-b]pyridazine with pyrrolidine bearing 4-phenyl-1,2,3-triazole | 0.3 |
| 60 | (3,4-dimethoxyphenyl)-imidazo[1,2-b]pyridazine with pyrrolidine bearing OAc | 0.4 |
| 61 | (3,4-dimethoxyphenyl)-imidazo[1,2-b]pyridazine with pyrrolidine bearing NHAc | 0.9 |

TABLE 1A-continued

Representative Inhibitors of nSMase2 of Formula (I)

| Entry | Structure | IC$_{50}$ (μM) |
|---|---|---|
| 62 | (structure: 3-methyl-6-(4-methylphenyl)-7-(3,4-dimethoxyphenyl)-imidazo[1,2-b]pyridazine with pyrrolidinyl-NHAc substituent) | 0.05 |
| 63 | (structure: cyclohexyl ketone-piperazinyl-dimethyl-imidazo[1,2-b]pyridazine with 3,4-dimethoxyphenyl) | 2 |
| 64 | (structure: dimethyl-imidazo[1,2-b]pyridazine with pyrrolidinyl-NHAc and N-methylindole substituent) | 1 |
| 65 | (structure: triazolopyrimidine with pyrrolidinyl-NHAc and 3,4-dimethoxyphenyl) | 100 |
| 9-PROV | (structure: 6-chloro-2-methyl-imidazo[1,2-b]pyridazine with pyrrolidinyl-NHAc) | >100 |
| 11-PROV | (structure: 6-chloro-2-methyl-3-(4-methoxyphenyl)-imidazo[1,2-b]pyridazine with pyrrolidinyl-NHAc) | >100 |
| 14-PROV | (structure: 6-chloro-2-methyl-3-(3-methoxyphenyl)-imidazo[1,2-b]pyridazine with pyrrolidinyl-NHAc) | >100 |

TABLE 1A-continued

Representative Inhibitors of nSMase2 of Formula (I)

| Entry | Structure | IC$_{50}$ (μM) |
|---|---|---|
| 15-PROV | 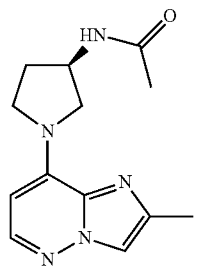 [SMILES: CC(=O)N[C@@H]1CCN(c2ccnn3cc(C)nc23)C1] | >10 |
| 18-PROV | 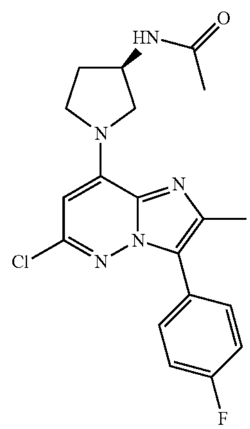 [SMILES: CC(=O)N[C@@H]1CCN(c2cc(Cl)nn3c(-c4ccc(F)cc4)c(C)nc23)C1] | >100 |
| 19-PROV | 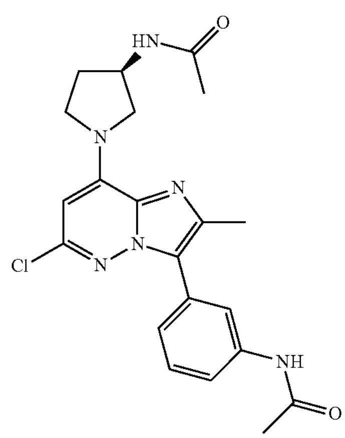 [SMILES: CC(=O)Nc1cccc(-c2c(C)nc3c(N4CC[C@@H](NC(C)=O)C4)cc(Cl)nn23)c1] | >100 |
| 20-PROV | 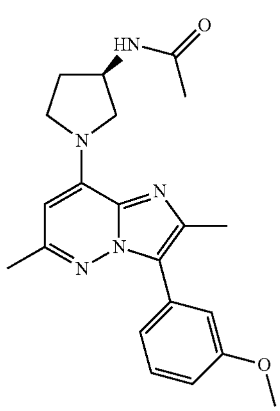 | >1 |
| 22-PROV | | >1 |
| 23-PROV | | >10 |
| 33-PROV | | >1 |

TABLE 1A-continued

Representative Inhibitors of nSMase2 of Formula (I)

| Entry | Structure | IC$_{50}$ (μM) |
|---|---|---|
| 38-PROV | 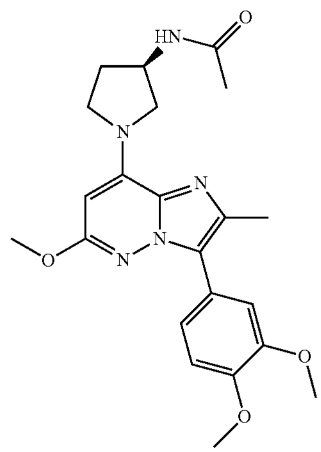 | >1 |
| 39b-PROV | 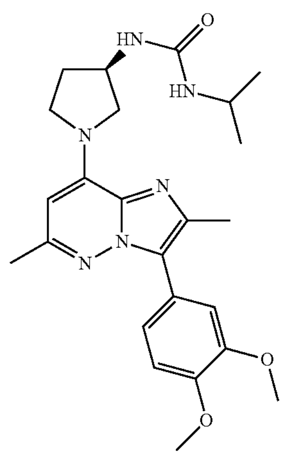 | ≤1 |
| 40-PROV | 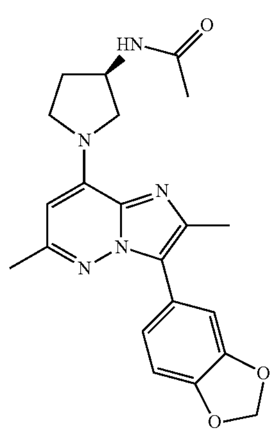 [SMILES: CC(=O)N[C@@H]1CCN(c2cc(C)nn3c(-c4ccc5c(c4)OCO5)c(C)nc23)C1] | ≤1 |
| 42-PROV | | >1 |
| 43-PROV | | ≤1 |
| 44-PROV | | >1 |

TABLE 1A-continued

Representative Inhibitors of nSMase2 of Formula (I)

| Entry | Structure | IC$_{50}$ (μM) |
|---|---|---|
| 46-PROV | 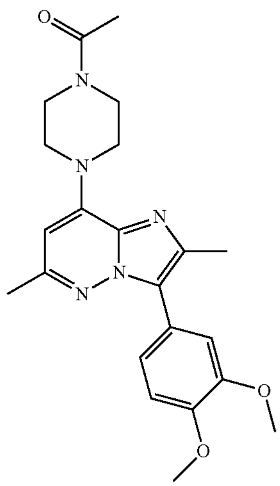 | >1 |
| 47-PROV | 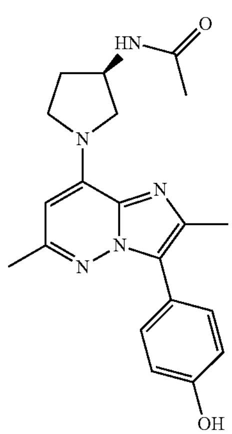 | ≤1 |
| 48-PROV | 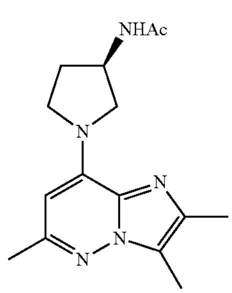 | >1 |
| 50-PROV | | — |
| 54-PROV | | — |
| 56-PROV | | — |

TABLE 1A-continued

Representative Inhibitors of nSMase2 of Formula (I)

| Entry | Structure | IC$_{50}$ (μM) |
|---|---|---|
| 59-PROV | 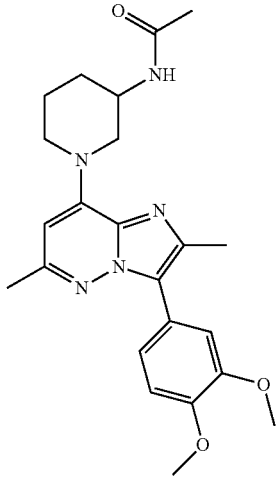 | — |

In other embodiments, the presently disclosed subject matter provides a method for treating a Human Immunodeficiency Virus (HIV) infection, the method comprising administering to a subject in need of treatment thereof an effective amount of an nSMase2 inhibitor of formula (II):

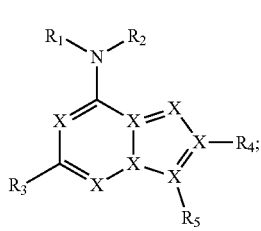

(II)

wherein: each X is independently selected from the group consisting of C(H)$_{0-1}$, N, O, and S; $R_1$ and $R_2$ together with the nitrogen atom to which they are bound form a substituted or unsubstituted 5- or 6-membered heterocyclic ring; $R_3$ is selected from the group consisting of H, substituted or unsubstituted alkyl, substituted or unsubstituted alkoxyl, substituted or unsubstituted thioalkyl, substituted or unsubstituted aryl, and halogen; $R_4$ can be present or absent and when present is selected from the group consisting of H, substituted or unsubstituted alkyl; $R_5$ is selected from the group consisting of H, halogen, substituted or unsubstituted aryl, substituted or unsubstituted heteroaryl, and a substituted or unsubstituted multicyclic aryl or heteroaryl ring; and pharmaceutically acceptable salts thereof.

In some embodiments, the compound of formula (II) is selected from the group consisting of:

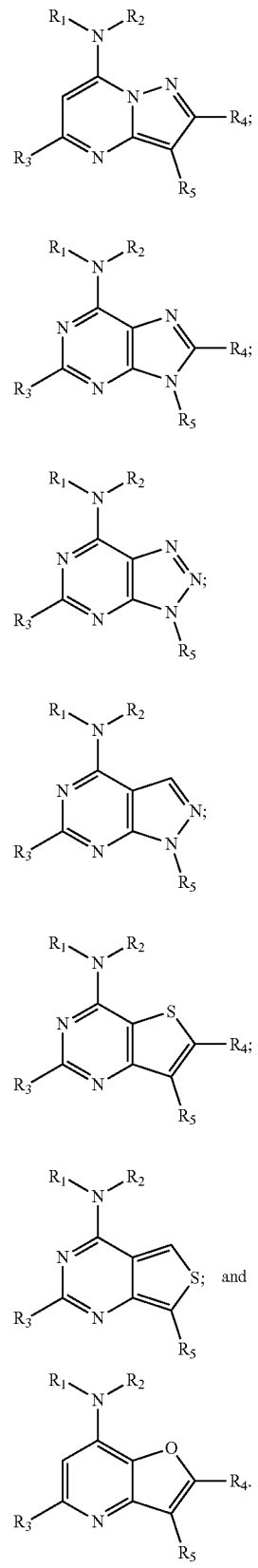

Representative compounds of formula (II) and their activities are summarized in Table 1B.

TABLE 1B

Representative Inhibitors of nSMase2 of Formula (II)

| No | Code | Structure | Activity* | MW |
|---|---|---|---|---|
| 1-PROV | MS-796 | 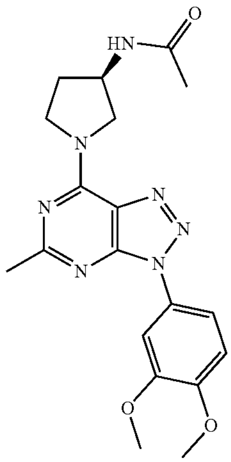 [SMILES: COc1ccc(-n2nnc3c(N4CC[C@@H](NC(C)=O)C4)nc(C)nc32)cc1OC] | D | 397.43 |
| 2-PROV | MS 797 | 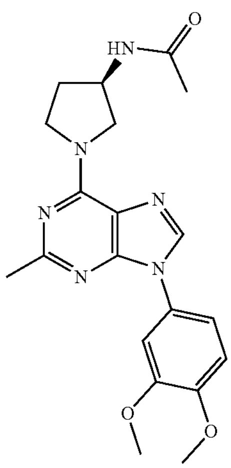 [SMILES: COc1ccc(-n2cnc3c(N4CC[C@@H](NC(C)=O)C4)nc(C)nc32)cc1OC] | D | 396.44 |
| 3-PROV | MS 798 | 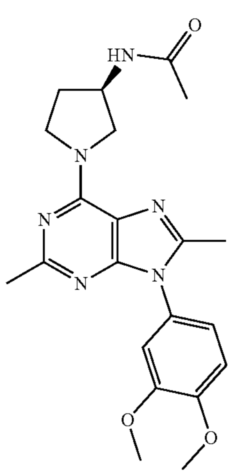 [SMILES: COc1ccc(-n2c(C)nc3c(N4CC[C@@H](NC(C)=O)C4)nc(C)nc32)cc1OC] | D | 410.47 |
| 4-PROV | MS 799 | | D | 409.48 |
| 5-PROV | MS 800 | | D | 396.44 |
| 6-PROV | MS 801 | | D | 382.42 |

TABLE 1B-continued

Representative Inhibitors of nSMase2 of Formula (II)

| No | Code | Structure | Activity* | MW |
|---|---|---|---|---|
| 7-PROV | MS 799A | 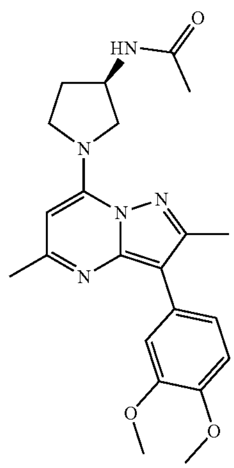 [SMILES: COc1ccc(-c2c(C)nn3c(N4CC[C@@H](NC(C)=O)C4)cc(C)nc23)cc1OC] | D | 409.48 |
| 8-PROV | MS 803 | 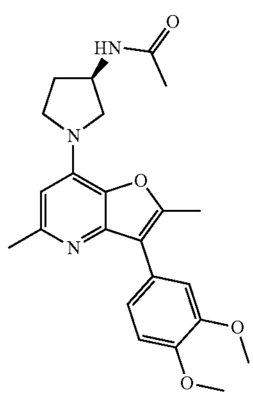 | D | 409.48 |
| 10-PROV | MS 805 | 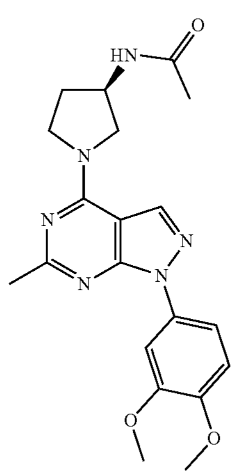 [SMILES: COc1ccc(-n2ncc3c(N4CC[C@@H](NC(C)=O)C4)nc(C)nc32)cc1OC] | D | 396.44 |
| 12-PROV | MS 807 | 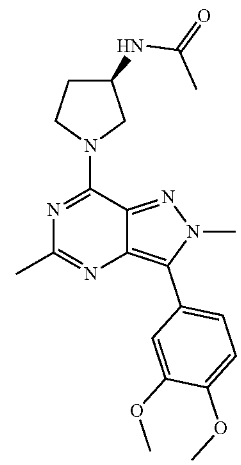 [SMILES: COc1ccc(-c2c3nc(C)nc(N4CC[C@@H](NC(C)=O)C4)c3nn2C)cc1OC] | D | 410.47 |
| 13-PROV | MS 808 | 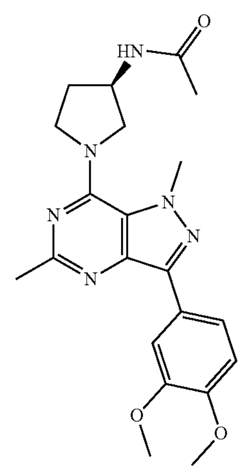 [SMILES: COc1ccc(-c2nn(C)c3c(N4CC[C@@H](NC(C)=O)C4)nc(C)nc23)cc1OC] | D | 410.47 |
| 24-PROV | HH 1280 | 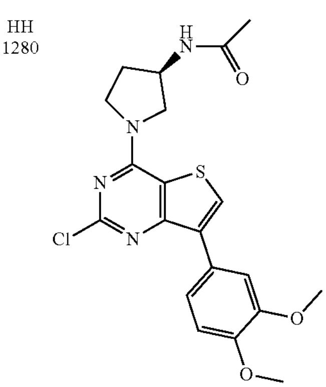 | D | 432.92 |

TABLE 1B-continued

Representative Inhibitors of nSMase2 of Formula (II)

| No | Code | Structure | Activity* | MW |
|---|---|---|---|---|
| 25-PROV | HH 1281 | 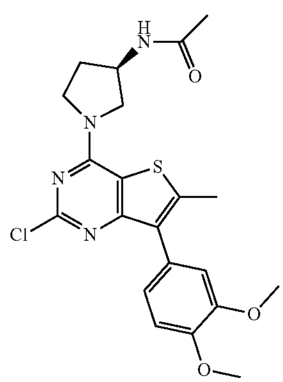 [SMILES: COc1ccc(-c2c(C)sc3c(N4CC[C@@H](NC(C)=O)C4)nc(Cl)nc23)cc1OC] | D | 446.95 |
| 26-PROV | HH 1283 | 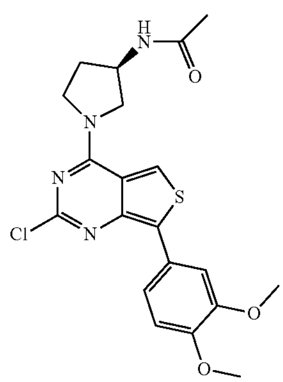 [SMILES: COc1ccc(-c2scc3c(N4CC[C@@H](NC(C)=O)C4)nc(Cl)nc23)cc1OC] | D | 432.92 |
| 27-PROV | HH 1284 | 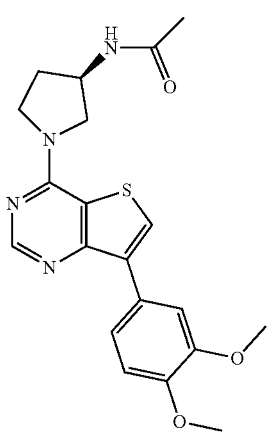 [SMILES: COc1ccc(-c2csc3c(N4CC[C@@H](NC(C)=O)C4)ncnc23)cc1OC] | D | 398.48 |
| 28-PROV | HH 1287 | 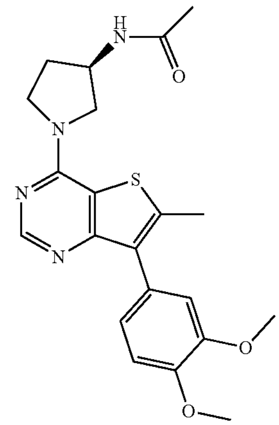 [SMILES: COc1ccc(-c2c(C)sc3c(N4CC[C@@H](NC(C)=O)C4)ncnc23)cc1OC] | D | 412.51 |
| 29a-PROV | HH 1288 | 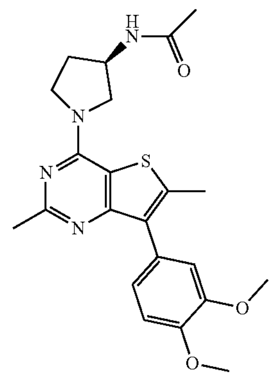 | D | 426.54 |
| 29b-PROV | HH 1289 | 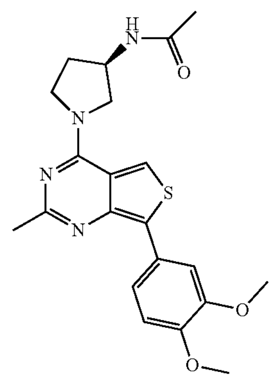 | D | 412.51 |
| 30-PROV | HH 1290 | 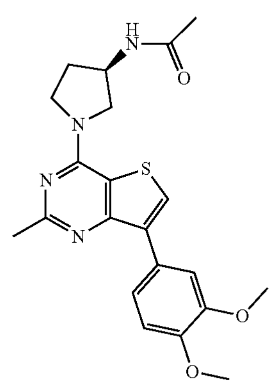 | D | 412.51 |

TABLE 1B-continued

Representative Inhibitors of nSMase2 of Formula (II)

| No | Code | Structure | Activity* | MW |
|---|---|---|---|---|
| 36-PROV | MS 824 | 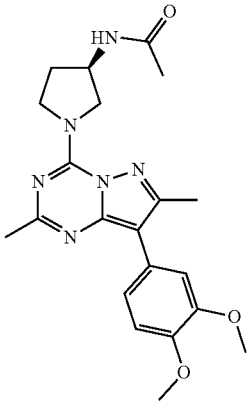 | D | 410.47 |

*The activities of the compounds are scaled into four groups (A-D) as follows:
Category D $IC_{50}$ >100 μM;
Category C $IC_{50}$ >10 μM;
Category B $IC_{50}$ >1 μM;
Category A $IC_{50}$ ≤1 μM.

In other embodiments, the presently disclosed subject matter provides a method for treating a Human Immunodeficiency Virus (HIV) infection, the method comprising administering to a subject in need of treatment thereof an effective amount of 2,6-dimethoxy-4-(5-phenyl-4-thiophen-2-yl-1H-imidazol-2-yl)-phenol (DPTIP):

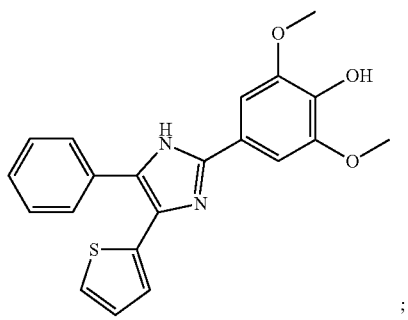 [SMILES: COc1cc(-c2nc(-c3cccs3)c(-c3ccccc3)[nH]2)cc(OC)c1O]

or a pharmaceutically acceptable salt thereof.

In some embodiments, the administration of an effective amount of an nSMase2 inhibitor of formula (I) or formula (II) or DPTIP interferes with the HIV life cycle.

Generally, the stages of the HIV life cycle include binding, fusion, reverse transcription, integration, replication, assembly, and budding. In the binding stage, HIV binds to receptors on the outer surface of a CD4 cell. Once attached, the HIV envelope and the CD4 cell membrane fuse, i.e., the fusion stage, which allows HIV to enter the CD4 cell. Once inside the CD4 cell, HIV releases reverse transcriptase, which converts its genetic material, HIV RNA, into HIV DNA. The conversion of HIV RNA to HIV DNA allows HIV to enter the CD4 cell nucleus and combine with the cell's genetic material (cell DNA). Once inside the CD4 cell nucleus, during the integration stage, HIV releases integrase to insert, or integrate, its viral DNA into the DNA of the CD4 cell. Once integrated into the CD4 cell DNA, HIV begins to use the machinery of the CD4 cell to make long chains of HIV proteins. The protein chains are the building blocks for more HIV. During the assembly stage, new HIV proteins and HIV RNA move to the surface of the cell and assemble into immature (noninfectious) HIV. During the buddy stage, newly formed immature (noninfectious) HIV pushes itself out of the host CD4 cell. The new HIV releases protease, which acts to break up the long protein chains that form the immature virus. The smaller HIV proteins combine to form mature, infectious, HIV.

In particular embodiments, the administration of an effective amount of an nSMase2 inhibitor of formula (I) or formula (II) or DPTIP blocks replication of the Human Immunodeficiency Virus (HIV). In yet more particular embodiments, the administration of an effective amount of an nSMase2 inhibitor of formula (I) or formula (II) or DPTIP prevents HIV viral assembly. In even yet more particular embodiments, the administration of an effective amount of an nSMase2 inhibitor of formula (I) or formula (II) or DPTIP prevents HIV budding. In certain embodiments, the administration of an effective amount of an nSMase2 inhibitor of formula (I) or formula (II) or DPTIP prevents viral replication by blocking HIV budding from HIV-infected cells in the subject.

In certain embodiments, the administration of an effective amount of a compound of formula (I) or formula (II) or DPTIP to the subject decreases or inhibits the (nSMase2) activity or expression in the subject.

As used herein, the term "inhibit," and grammatical derivations thereof, refers to the ability of a presently disclosed compound, e.g., a presently disclosed compound of formula (I) or formula (II) or DPTIP, to block, partially block, interfere, decrease, or reduce the growth of bacteria or a bacterial infection. Thus, one of ordinary skill in the art would appreciate that the term "inhibit" encompasses a complete and/or partial decrease in the growth of bacteria or a bacterial infection, e.g., a decrease by at least 10%, in some embodiments, a decrease by at least 20%, 30%, 50%, 75%, 95%, 98%, and up to and including 100%.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of formula (I) and at least one other active agent. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) or formula (II) or DPTIP described herein can be administered alone or in combination with adjuvants that enhance stability of the compounds of formula (I) or formula (II) or DPTIP, alone or in combination with one or more active agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) or formula (II) or DPTIP and at least one additional therapeutic agent can be varied so long as the beneficial effects of the combination of these agents are achieved. Accordingly, the phrase "in combination with" refers to the administration of a compound of formula (I) or formula (II) or DPTIP and at least one additional therapeutic agent either simultaneously, sequentially, or a combination thereof. Therefore, a subject administered a combination of a compound of formula (I) or formula (II) or DPTIP and at least one additional therapeutic agent can receive compound of formula (I) or formula (II) or DPTIP and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) or formula (II) or DPTIP and at least one additional therapeutic agent are administered simultaneously, they can be administered to the subject as separate pharmaceutical compositions, each comprising either a compound of formula (I) or formula (II) or DPTIP or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index (SI)}$$

wherein:
$Q_A$ is the concentration of a component A, acting alone, which produced an end point in relation to component A;
$Q_a$ is the concentration of component A, in a mixture, which produced an end point;
$Q_B$ is the concentration of a component B, acting alone, which produced an end point in relation to component B; and
$Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

D. Pharmaceutical Compositions and Administration

In another aspect, the present disclosure provides a pharmaceutical composition including one compound of formula (I) or formula (II) or DPTIP alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) 0, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$CH_2CH_2CH_2CH_2$—, —$CH_2CH$═$CHCH_2$—, —$CH_2C_5CCH_2$—, —$CH_2CH_2CH$ ($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

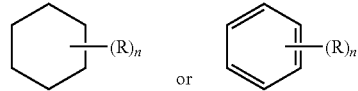

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

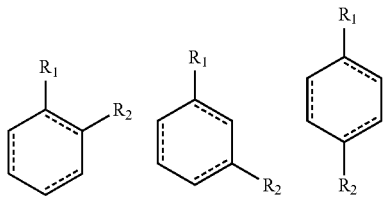

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ($\sim\!\!\sim\!\!\sim\!\!\sim$) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO₂R', —C(O)NR'R", —OC(O)NR'R", —NR"C(O)R', —NR'—C(O)NR"R'", —NR"C(O)OR', —NR—C(NR'R")=NR'", —S(O)R', —S(O)₂R', —S(O)₂NR'R", —NRSO₂R', —CN, CF₃, fluorinated C$_{1-4}$ alkyl, and —NO₂ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO₂R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)₂R', —S(O)₂NR'R", —NRSO₂R', —CN and —NO₂, —R', —N₃, —CH(Ph)₂, fluoro(C$_{1-4}$)alkoxo, and fluoro(C$_{1-4}$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R' and R"" groups when more than one of these groups is present.

Two of the substituents on adjacent atoms of aryl or heteroaryl ring may optionally form a ring of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)₂—, or —S(O)₂NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R' are each independently selected from the group consisting of alkyl groups. Additionally, R', R", and/or R'"taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

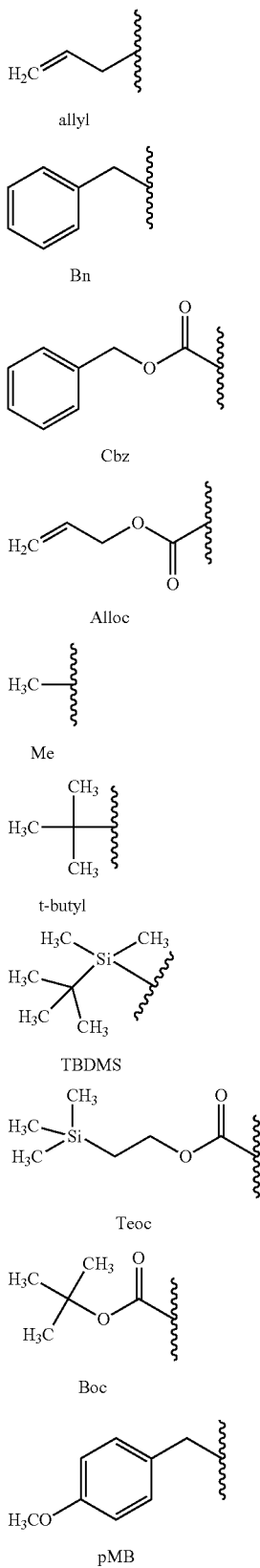

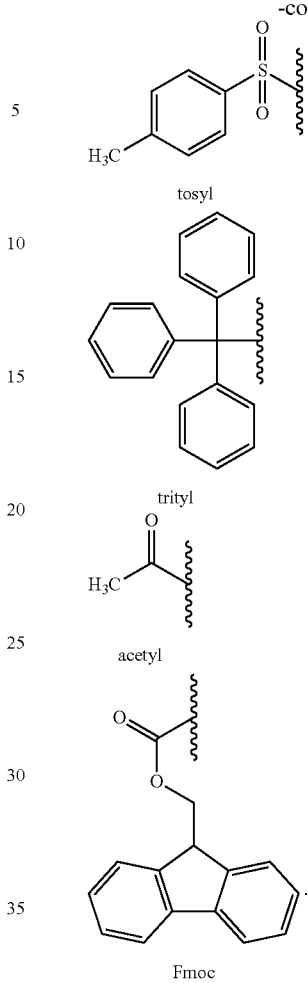

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

HIV Infection

H9 cells were infected with 100 ng/mL of HIV Rf (NIH AIDS repository) at 37° C. for 4 h. Cells were then washed twice with sf-medium (Gibco), and cultured in fresh R10 medium at density of $1 \times 10^6$/mL. On day 3, HIV-infection was confirmed by P24 ELISA. On day 7, HIV-infected H9 cells were harvested and resuspended at density $3 \times 10^5$/mL in 24-well tissue culture plates with volume of 1 mL/well. A dose response of nSMase inhibitors, and inactive analogs were added to the cultures (100, 60, 30, 10, 1, 0.3, 0.1, and 0.03 μM). Controls included no-treatment and vehicle. Cell viability and P24 were measured every 24 h for 4 days.

Example 2

Early Stages of Viral Infection

To assess the potential of nSMase inhibitors to interfere with HIV life cycle stages from attachment and entry through transcription, a luciferase assay was done using TZM/B1 cells (NIH AIDS repository) that measures infection as function of reductions in HIV-1 Tat-regulated firefly luciferase (Luc) reporter gene expression.

Example 3

Humanization of Mice

Immunodeficient NSG (NOD.Cg-Prkdc$^{scid}$ Il2rg$^{tm1Wjl}$/SzJ) mice (Jackson Laboratories) were exposed to γ-irradiation (10Gy, 137Ce source) at postnatal day 0 and injected intrahepatic with $2.0 \times 10^5$ human umbilical cord blood-derived CD34+ hematopoietic stem cells (Stem Cell Technology, Lot #. 1603160112). Humanization of NSG mice was determined 20 weeks following transplantation by flow cytometry (Miltenyl Biotec) using human specific antibodies directed against hCD45-APC (Leukocytes; Thermo Fisher), hCD3-PE (T cells; Biolegend), hCD14-PE/Cy7 (Macrophage; Biolegend), hCD19-BV421 (B cells; Biolegend). Percent humanization was calculated as a ratio for each of the human antibodies to a mouse specific antibody directed against mCD45-FITC (eBioscience). Mice >5% humanization (in each cell category) were included for experiments.

Example 4

HIV Infection/Validation of HIV Infection

Mice were intraperitoneally infected with HIV1-Ada (10,000 TCID$_{50}$) 20-22 weeks following transplantation, and plasma viral loads measured weekly. Viral RNA was isolated using the QIAamp viral RNA mini kit (Qiagen), reverse transcribed, and cDNAs amplified using forward primer 5'-GTCTGCGTCATCTGGTGCATTC-3' (SEQ ID NO: 1), reverse primer 5'-CACTAGGTGTCTCTGCAC-TATCTGTTTTG-3' (SEQ ID NO: 2) and probe 5'-(FAM) CTTCCTCAGTGTGTTTCACTTTCTCTTCTG (BHQ_1)-3' (SEQ ID NO: 3). Reaction included a non-template control, non-enzyme control and sample was analyzed on an Applied Biosystem 7300 Real-Time PCR system (Life Technology). Cycling parameters were as follows: 1 cycle at 50° C. for 30 min, 1 cycle at 95° C. for 15 min, 45 cycles of 94° C. for 15 sec, and 55° C. for 30 sec, 60° C. for 30 sec. The dissociation stage was 95° C. for 15 sec, 60° C. for 1 min and 95° C. for 15 sec.

Example 5

Drug Treatments

Experimental drugs were delivered intraperitoneally at a dose of 10 mg/kg once daily beginning 5 weeks after HIV infection for a duration of 6 weeks. Drugs were reconstituted in 5% DMSO, 5% Tween-80 and 90% saline. Control mice injected with vehicle consisting of 5% DMSO, 5% Tween-80 in saline. Inhibitors tested in these studies include JHU 3399, JHU 3398, MS796 (1-PROV) and MS822 (31).

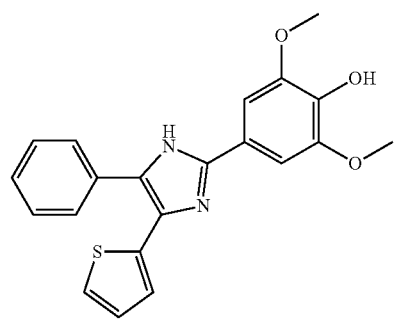

JHU 3399

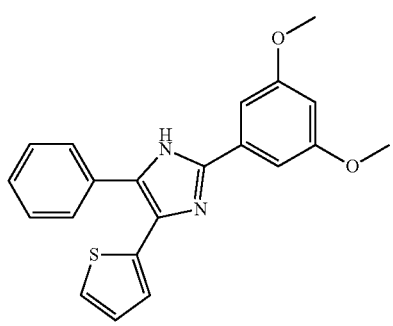

JHU 3398

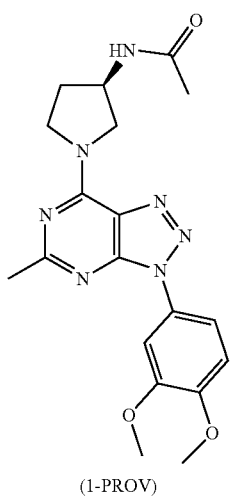

(1-PROV)

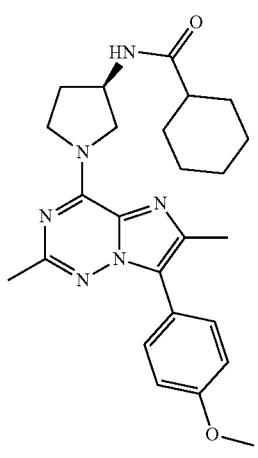

(31)

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Bowes, J., Brown, A. J., Hamon, J., Jarolimek, W., Sridhar, A., Waldron, G., and Whitebread, S. (2012) Reducing safety-related drug attrition: the use of in vitro pharmacological profiling, Nat Rev Drug Discov 11, 909-922.

Dickens, A. M., Tovar, Y. R. L. B., Yoo, S. W., Trout, A. L., Bae, M., Kanmogne, M., Megra, B., Williams, D. W., Witwer, K. W., Gacias, M., Tabatadze, N., Cole, R. N., Casaccia, P., Berman, J. W., Anthony, D. C., and Haughey, N. J. (2017) Astrocyte-shed extracellular vesicles regulate the peripheral leukocyte response to inflammatory brain lesions, Sci Signal 10.

Figuera-Losada, M., Stathis, M., Dorskind, J. M., Thomas, A. G., Bandaru, V. V., Yoo, S. W., Westwood, N. J., Rogers, G. W., McArthur, J. C., Haughey, N. J., Slusher, B. S., and Rojas, C. (2015) Cambinol, a novel inhibitor of neutral sphingomyelinase 2 shows neuroprotective properties, PLoS One 10, e0124481.

McCluskey, L., Campbell, S., Anthony, D., and Allan, S. M. (2008) Inflammatory responses in the rat brain in response to different methods of intra-cerebral administration, J Neuroimmunol 194, 27-33.

Rais, R., Jancarik, A., Tenora, L., Nedelcovych, M., Alt, J., Englert, J., Rojas, C., Le, A., Elgogary, A., Tan, J., Monincova, L., Pate, K., Adams, R., Ferraris, D., Powell, J., Majer, P., and Slusher, B. S. (2016) Discovery of 6-Diazo-5-oxo-1-norleucine (DON) Prodrugs with Enhanced CSF Delivery in Monkeys: A Potential Treatment for Glioblastoma, J Med Chem 59, 8621-8633.

Loberto, C., Hasslere, D. F., Signorelli, P., Okamoto, Y., Sawai, H., Boros, E., Hazen-Martin, D. J., Obeid, L. M., Hannun, Y. A., and Smith, G. K., "Inibition of Tumor Necrosis Factor-induced Cell Death in MCF7 by a Novel Inhibitor of Neutral Sphingomyelinase" J Biol Chem Vol. 277, 41128-41139 (2002).

Figuera-Losada, M., Stathis, M., Dorskind, J. M., Thomas, A. G., Bandaru, V. Yoo, S.-W., Westwood, N. J., Rogers, G. W., McArthur, J. C., Haughey, N. J., Slusher, B. S., and Rojas, C., Cambinol, a Novel Inhibitor of Neutral Sphingomyelinase 2 Shows Neuroprotective Properties, PLOS ONE, 26 May 2015.

Asai, H., Ikezu, S., Tsunoda, S., Medalla, M., Luebke, J., Haydar, T., Wolozin, B., Butovsky, O., Kugler, S., Ikezu, T., "Depletion of Microglia and Inhibition of Exosome Synthesis Halt Tau Propagation" Nat Neurosci Vol. 18, 1584-1593 (2015).

Van Echten-Deckert, G. and Walter, J. "Sphingolipids: Critical Players in Alzheimer's Disease" Progress in Lipid Research Vol. 51, 378-393 (2012).

Jana, A. and Pahan, K., "Fibrillar Amyloid-Beta-Activated Human Astroglia Kill Primary Human Neurons Via Neutral Sphingomyelinase: Implications for Alzheimer's Disease" J Neurosci Vol. 30, 12676-12689 (2010).

Jana, A. and Pahan, K., "Sphingolipids in Multiple Sclerosis" Neuromol Med Vol. 12, 351-361 (2010).

Jana, A., Hogan, E. L., Pahan, K., "Ceramide and Neurodegeneration: Susceptibility of Neurons and Oligodendrocytes to Cell Damage and Death" Journal of the Neurological Sciences Vol. 278, 5-15 (2009).

Cutler, R. G., Pedersen, W. A., Camandola, S., Rothstein, J. D., Mattson, M. P. "Evidence that Accumulation of Ceramides and Cholesterol Esters Mediates Oxidative Stree-Induced Death of Motor Neurons in Amyotrophic Lateral Sclerosis" Ann Neurol Vol. 52, 448-457 (2002).

Jana, A. and Pahan, K., "Human Immunodeficiency Virus Type 1 gp120 Induces Apoptosis in Human Primary Neurons through Redox-Regulated Activation of Neutral Sphingomyelinase" J Neurosci Vol. 24, 9531-9540 (2004).

Haughey, N. J., Cutler, R. G., Tamara, A., McArthur, J. C., Vargas, D. L., Pardo, C. A., Turchan, J., Nath, A., Mattson, M. P. "Perturbation of Sphingolipid Metabolism and Ceramide Production in HIV-Dementia" Ann Neurol Vol. 55, 257-267 (2004).

Kosaka, N., Iguchi, H., Hagiwara, K., Yoshioka, Y., Takeshita, F., Ochiya, T., "Neutral Sphingomyelinase 2 (nSMase2)-dependent Exosomal Transfer of Angiogenic MicroRNAs Regulate Cancer Cell Metastasis" J Biol Chem Vol. 288, 10849-10859 (2013).

Horres, C. R. and Hannun, Y. A., "The Roles of Neutral Spingomyelinases in Neurological Pathologies" Neurochem Res Vol. 37, 1137-1149 (2012).

Mejdrova, I., Chalupska, D., Kogler, M., Sala, M., Plackova, P., Baumlova, A., Hrebabecky, H., Prochazkova, E., Dejmek, M., Guillon, R., Strunin, D., Weber. J., Lee, G., Birkus, G., Mertlikova-Kalserova, H., Boura, E., Nencka, R. "Highly Selective Phosphatidylinositol 4-Kinase III-Beta Inhibitors and Structural Insight Into Their Mode of Action" J. Med. Chem., Vol. 58, 3767-3793 (2015).

Sala, M., Kogler, M., Plackova, P., Mejdrova, I., Hrebabecky, H., Prochazkova, E., Strunin, D., Lee, G., Birkus, G., Weber, J., Mertlikova-Kaiserova, H., Nencka, R., "Purine Analogs as Phosphatidylinositol 4-Kinase IIIBeta Inhibitors" Bioorg. Med. Chem. Lett., Vol. 26, 2706-2712 (2016).

U.S. Patent Application Publication No. US20120220581A1 for Imidazo[1,2-b]pyridazine Derivatives and their use as PDE10 Inhibitors, to Pastor-Fernández, published Aug. 30, 2012.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a Human Immunodeficiency Virus (HIV) infection, the method comprising administering to a subject in need of treatment thereof an effective amount of an nSMase2 inhibitor of formula (I), wherein the compound of formula (I) is:

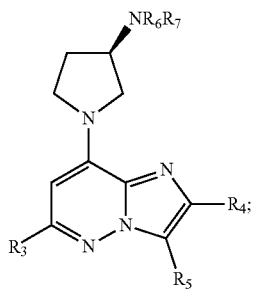

wherein:

$R_3$ is selected from the group consisting of substituted or unsubstituted alkyl, substituted or unsubstituted alkoxyl, substituted or unsubstituted thioalkyl, and substituted or unsubstituted aryl;

$R_4$ is selected from the group consisting of H, substituted or unsubstituted alkyl, and substituted or unsubstituted aryl;

$R_5$ is selected from the group consisting of substituted or unsubstituted aryl, substituted or unsubstituted heteroaryl, and a substituted or unsubstituted multicyclic aryl or multicyclic heteroaryl ring;

$R_6$ is selected from the group consisting of H or substituted or unsubstituted $C_{1-6}$ alkyl;

$R_7$ is selected from the group consisting of —C(=O)—$(CR_yR_z)_m$—$R_8$, —C(=O)—$(CR_yR_z)_m$—O—$R_8$, —C(=O)—O—$(CR_yR_z)_m$—$R_8$, and —S(=O)$_2$—$R_9$, wherein each m is an integer selected from the group consisting of 0, 1, 2, 3, 4, 5, and 6, $R_y$ and $R_z$ are each independently H, alkoxyl, or halogen, $R_8$ and $R_9$ are each independently selected from the group consisting of substituted or unsubstituted alkyl, —$CF_3$, substituted or unsubstituted cycloalkyl, substituted or unsubstituted aryl, substituted or unsubstituted cycloheteroaryl, substituted or unsubstituted multicyclic aryl or heteroaryl ring, and $NR_{10}R_{11}$, wherein $R_{10}$ and $R_{11}$ are each independently selected from the group consisting of H, substituted or unsubstituted $C_{1-6}$ alkyl, and substituted or unsubstituted aryl; and pharmaceutically acceptable salts thereof.

2. The method of claim 1, wherein the compound of formula (I) is:

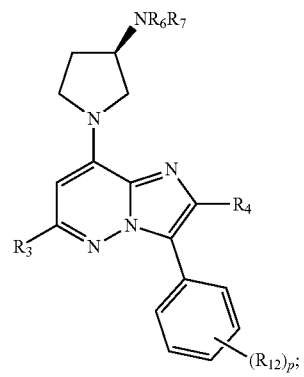

wherein:

p is an integer selected from the group consisting of 0, 1, 2, 3, 4, and 5;

each $R_{12}$ is independently selected from the group consisting of substituted or unsubstituted alkyl, hydroxyl, alkoxyl, halogen, cyano, amino, —$CF_3$, —O—$CF_3$, substituted or unsubstituted cycloheteroaklyl, —$NR_{13}$(C=O)$R_{14}$, —S(=O)$_2$—$R_{15}$, —S(=O)$_2$—$NR_{15}R_{16}$, —$SR_{16}$, —C(=O)—$R_{17}$, —C(=O)—O—$R_{18}$, and —C(=O)—$NR_{19}R_{20}$, wherein $R_{13}$ is selected from the group consisting of H or substituted or unsubstituted $C_{1-6}$ alkyl, $R_{14}$ is substituted or unsubstituted $C_{1-6}$ alkyl or —O—$R_{21}$, and $R_{15}$, $R_{16}$, $R_{17}$, $R_{18}$, $R_{19}$, $R_{20}$, $R_{21}$ are each independently H or substituted or unsubstituted $C_{1-6}$ alkyl.

3. The method of claim 2, wherein $R_6$ is H and $R_7$ is —C(=O)—$(CR_yR_z)_m$—$R_8$, wherein m is 0 and $R_8$ is $C_{1-6}$ alkyl.

4. The method of claim 3, wherein the compound of formula (I) is selected from the group consisting of:

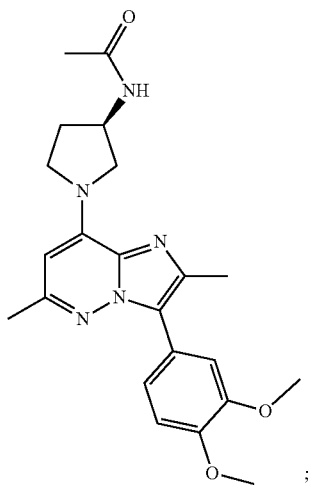
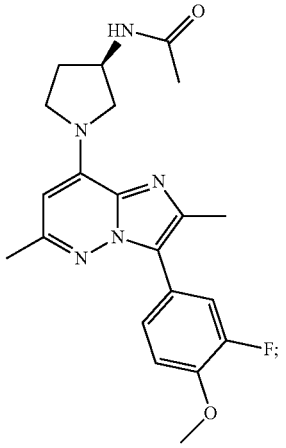
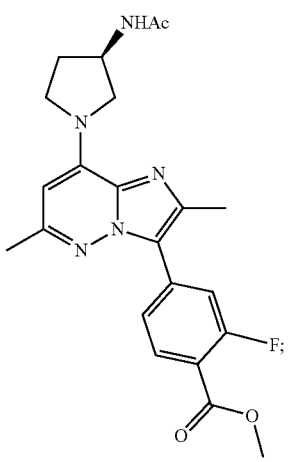
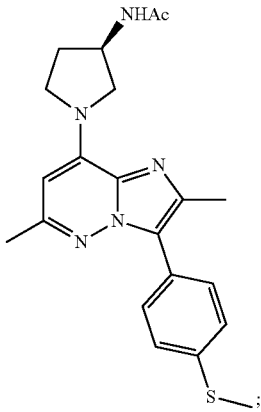
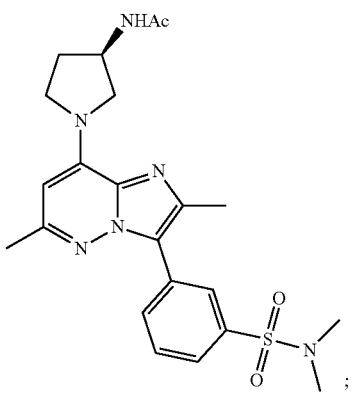

103
-continued
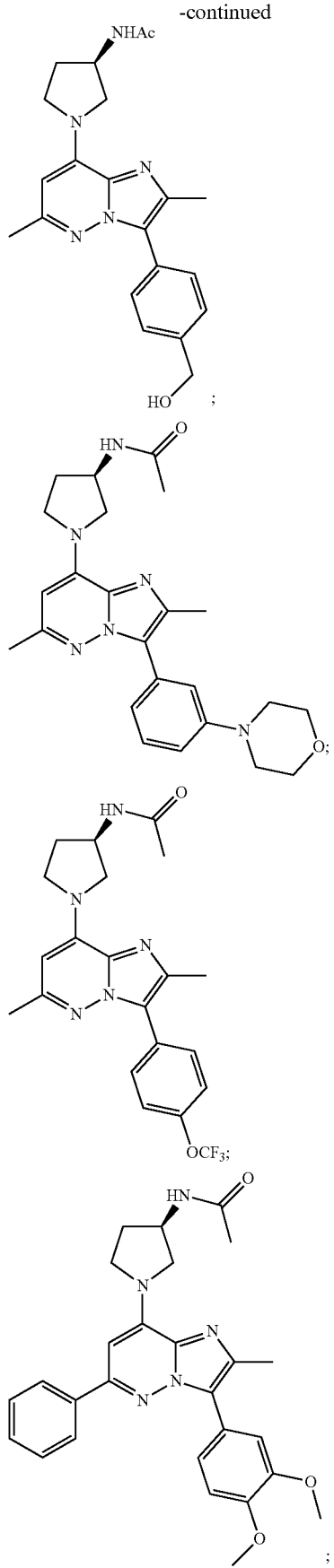
104
-continued
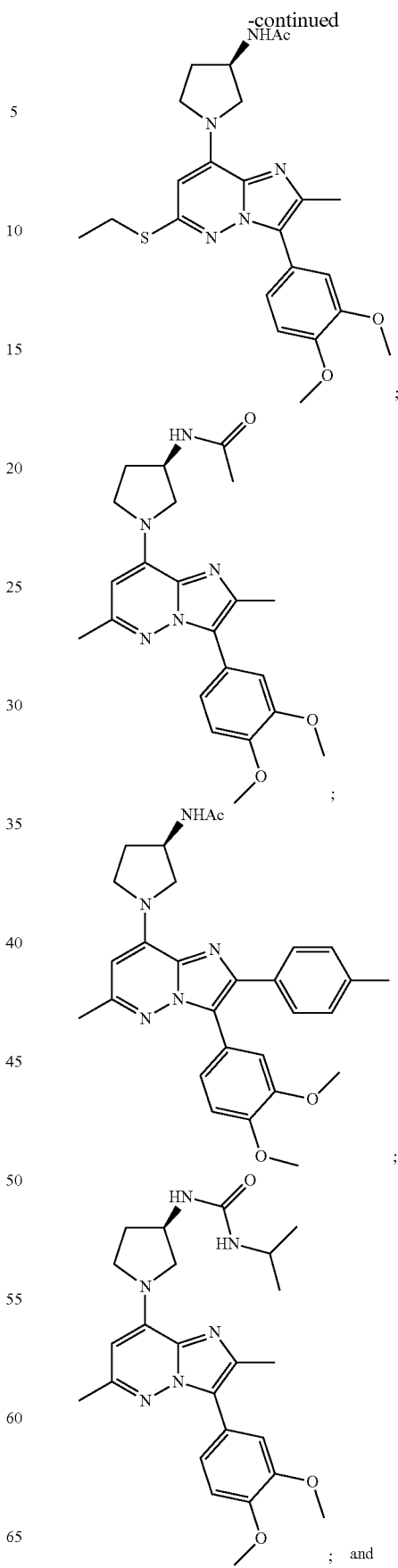
; and

-continued

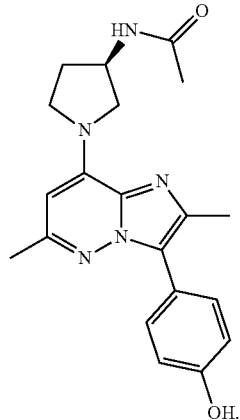

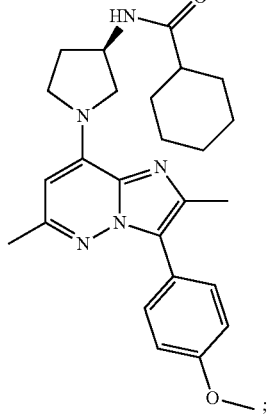

5. The method of claim 2, wherein $R_6$ is H and $R_7$ is selected from the group consisting of —C(=O)—(CR$_y$R$_z$)$_m$—R$_8$, —C(=O)—(CR$_y$R$_z$)$_m$—O—R$_8$, —C(=O)—O—(CR$_y$R$_z$)$_m$—R$_8$, wherein each m is an integer selected from the group consisting of 0, 1, 2, 3, 4, 5, and 6, $R_y$ and $R_z$ are each independently H, alkoxyl, or halogen, $R_8$ is selected from the group consisting of substituted or unsubstituted alkyl, —CF$_3$, substituted or unsubstituted cycloalkyl, substituted or unsubstituted aryl, substituted or unsubstituted cycloheteroaryl, substituted or unsubstituted multicyclic aryl or heteroaryl ring, and NR$_{10}$R$_{11}$, wherein $R_{10}$ and $R_{11}$ are each independently selected from the group consisting of H, substituted or unsubstituted C$_{1-6}$ alkyl, and substituted or unsubstituted aryl.

6. The method of claim 5, wherein the compound of formula (I) is selected from the group consisting of:

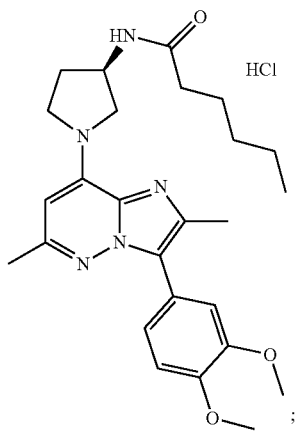

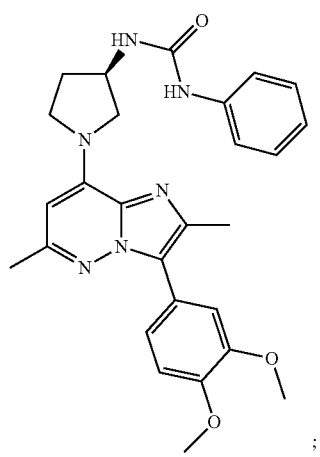

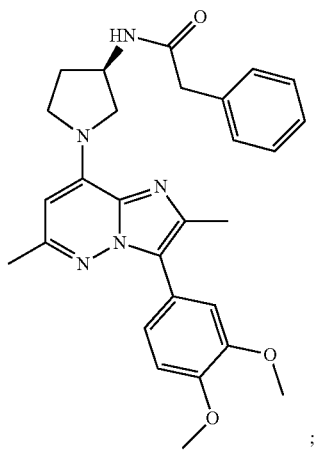

107
-continued
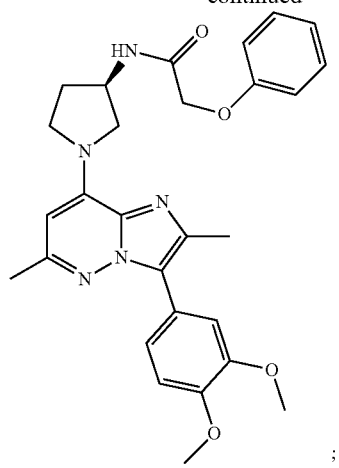
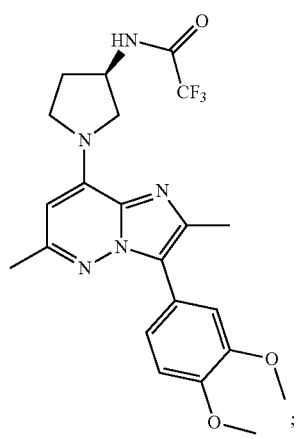
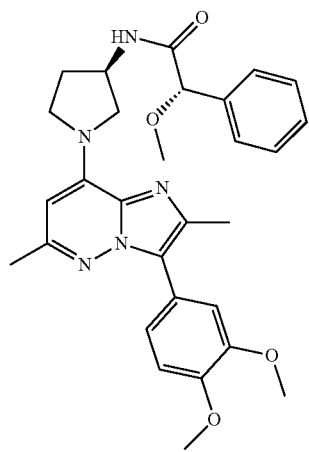
108
-continued
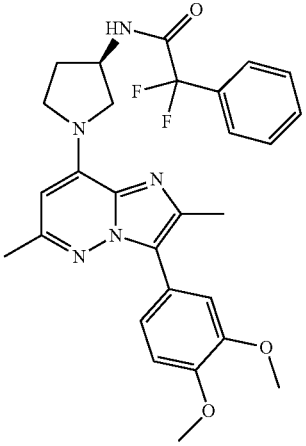
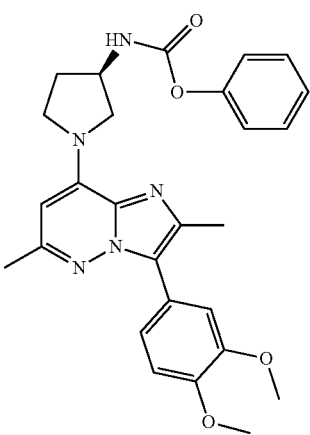
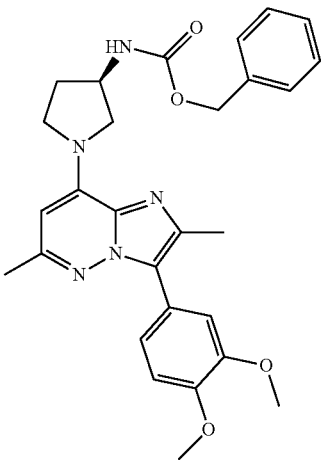

-continued
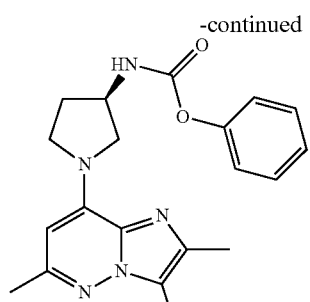
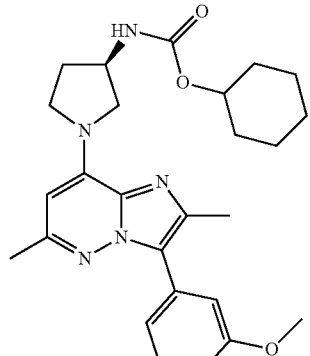
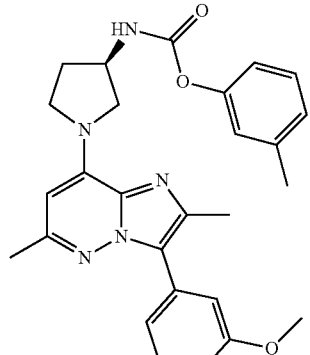
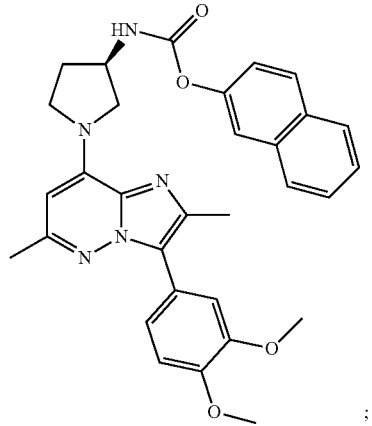
-continued
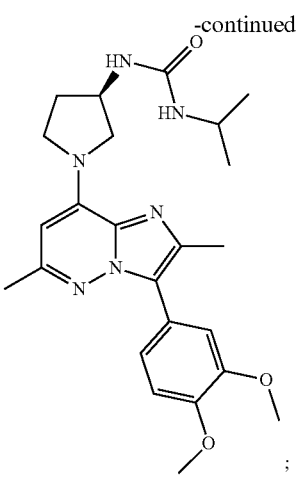
; and
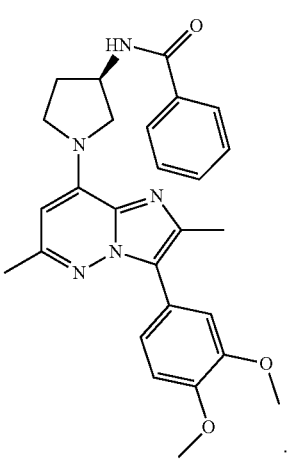
7. The method of claim 2, wherein $R_6$ is H and $R_7$ is $-S(=O)_2-R_9$.
8. The method of claim 5, wherein the compound of formula (I) is selected from the group consisting of:
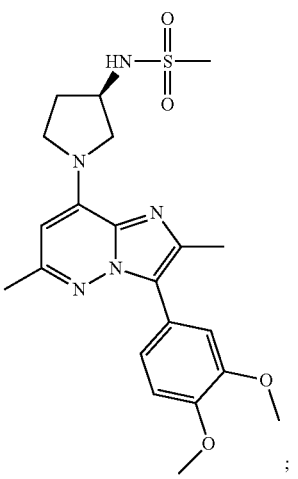
;

111
-continued
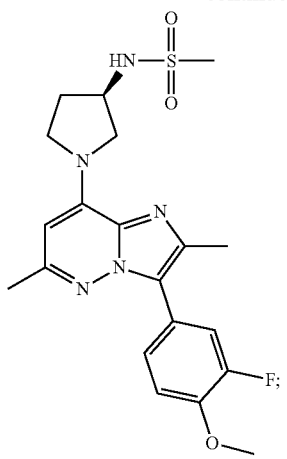
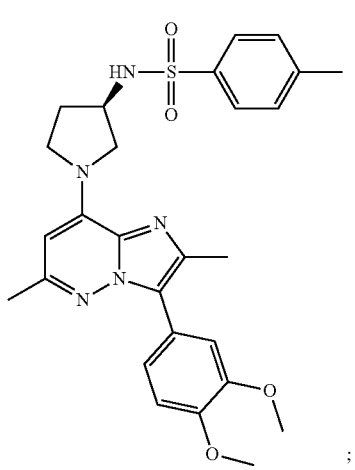
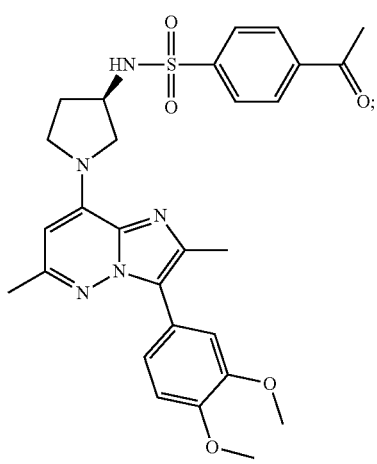
112
-continued
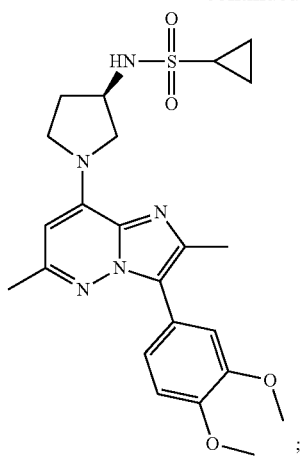
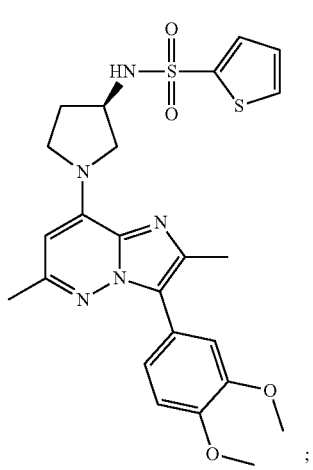
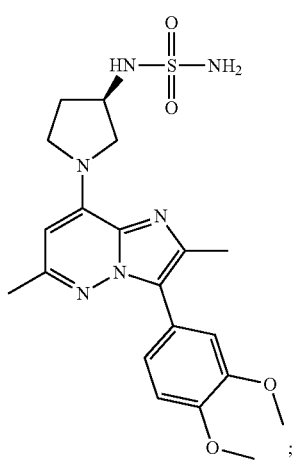

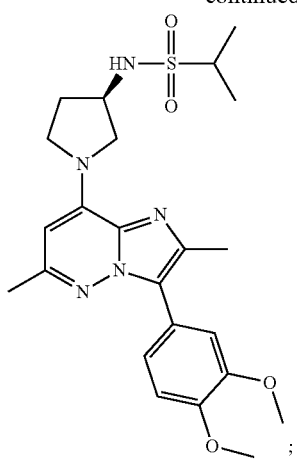
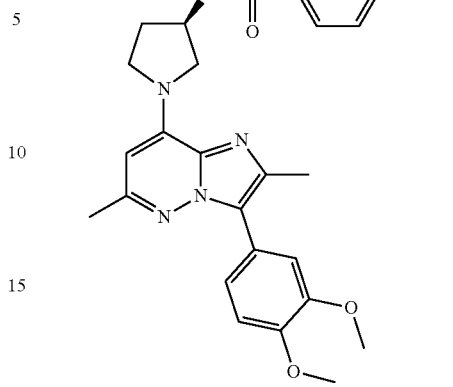
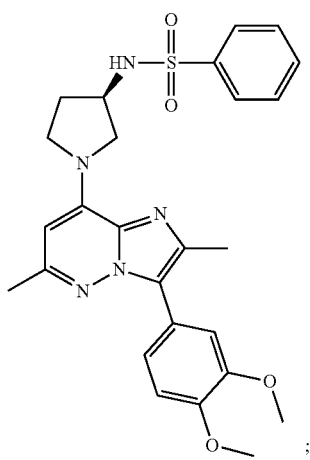
9. The method of claim 1, wherein $R_5$ is a substituted or unsubstituted multicyclic aryl or multicyclic heteroaryl ring.
10. The method of claim 9, wherein the compound of formula (I) is selected from the group consisting of:
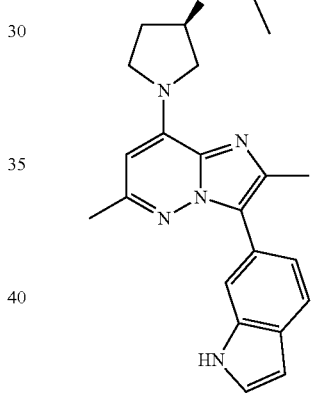
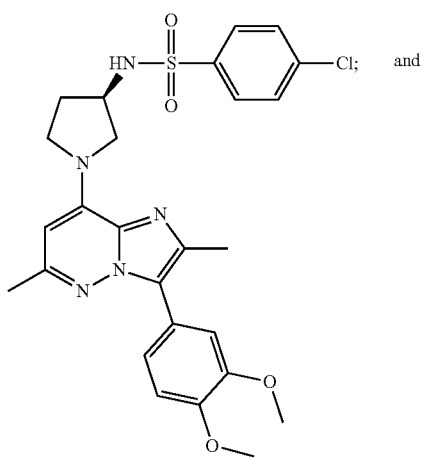
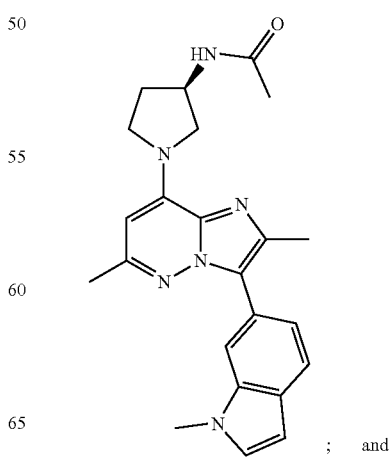
; and -continued

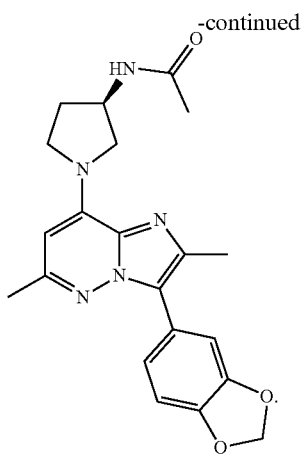

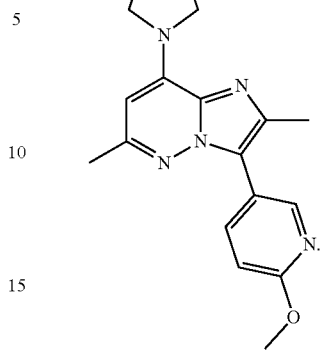

11. The method of claim 1, wherein R₅ is a substituted or unsubstituted heteroaryl.

12. The method of claim 11, wherein the compound of formula (I) is selected from the group consisting of:

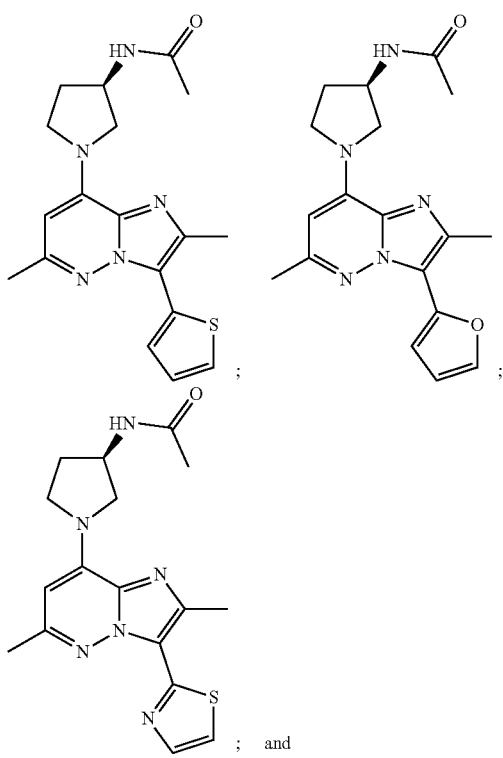

; and

13. The method of claim 1, wherein the administration of an effective amount of a compound of formula (I) to the subject has one or more effects selected from the group consisting of:
(a) decreases or inhibits the (nSMase2) activity in the subject;
(b) interferes with the HIV life cycle;
(c) blocks replication of the Human Immunodeficiency Virus (HIV);
(d) prevents HIV viral assembly;
(e) prevents HIV budding; and
(f) prevents viral replication by blocking HIV budding from HIV-infected cells in the subject.

14. The method of claim 6, wherein the compound of formula (I) is:

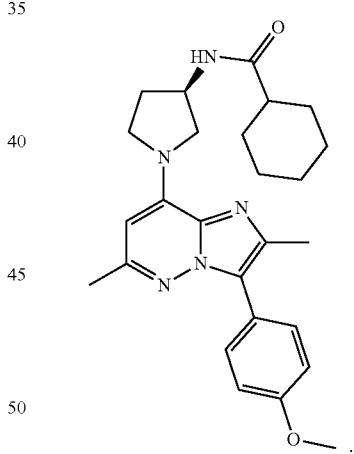

* * * * *